(12) United States Patent
Antoine et al.

(10) Patent No.: US 11,740,226 B2
(45) Date of Patent: Aug. 29, 2023

(54) DESIGNS AND FABRICATION OF NANOGAP SENSORS

(71) Applicant: Analog Devices International Unlimited Company, Limerick (IE)

(72) Inventors: Christophe Antoine, London (GB); Himanshu Jain, Norwood, MA (US); Matthew Thomas Canty, Nenagh (IE); Christina B. McLoughlin, Crecora (IE); Daniel Joseph Lucey, Limerick (IE); Sinead Maire McDermott, Oughterard (IE); Stephen O'Brien, Clarina (IE); Bernard Stenson, Limerick (IE); Shane Geary, Sixmilebridge (IE); William Allan Lane, Waterfall (IE); Michael Coln, Lexington, MA (US); Mark De Leon Alea, Manila (PH)

(73) Assignee: ANALOG DEVICES INTERNATIONAL UNLIMITED COMPANY, Limerick (IE)

( * ) Notice: Subject to any disclaimer, the term of this patent is extended or adjusted under 35 U.S.C. 154(b) by 57 days.

(21) Appl. No.: 16/651,832

(22) PCT Filed: Oct. 8, 2018

(86) PCT No.: PCT/EP2018/077272
§ 371 (c)(1),
(2) Date: Mar. 27, 2020

(87) PCT Pub. No.: WO2019/072743
PCT Pub. Date: Apr. 18, 2019

(65) Prior Publication Data
US 2020/0256842 A1 Aug. 13, 2020

Related U.S. Application Data

(60) Provisional application No. 62/571,921, filed on Oct. 13, 2017.

(51) Int. Cl.
*G01N 33/487* (2006.01)

(52) U.S. Cl.
CPC .............................. *G01N 33/48721* (2013.01)

(58) Field of Classification Search
CPC ........... G01N 33/48721; G01N 27/327; G01N 33/487; G01N 27/3278
See application file for complete search history.

(56) References Cited

U.S. PATENT DOCUMENTS 6,824,974 B2    11/2004  Pisharody et al.
7,220,345 B2     5/2007  Bohn et al.
(Continued)

FOREIGN PATENT DOCUMENTS

WO    WO-2015170783 A1 *  11/2015  ....... G01N 27/44791

OTHER PUBLICATIONS

Datar et al., *Cantilever Sensors: Nanomechanical Tools for Diagnostics*, MRS Bulletin, vol. 34, Jun. 2009, 7 pages.
(Continued)

*Primary Examiner* — Benjamin R Whatley
*Assistant Examiner* — Jean Caraballo-Leon
(74) *Attorney, Agent, or Firm* — ArentFox Schiff LLP

(57) ABSTRACT

Embodiments of the disclosure provide various nanogap sensor designs (e.g., horizontal nanogap sensors, vertical nanogap sensors, arrays of multiple nanogap sensors, various arrangements for making electrical connections to the electrodes of nanogap sensors, etc.), as well as various methods which may be used to fabricate at least some of the proposed sensors. The nanogap sensors proposed herein may operate as molecular sensors to help identify chemical species through electrical measurements using at least a pair of electrodes separated by a nanogap.

18 Claims, 22 Drawing Sheets

(56) References Cited

U.S. PATENT DOCUMENTS

| | | |
|---|---|---|
| 7,385,295 B2 | 6/2008 | Son et al. |
| 7,582,490 B2 | 9/2009 | Golovchenko et al. |
| 7,678,562 B2 | 3/2010 | Ling |
| 8,168,534 B2 | 5/2012 | Tang et al. |
| 8,304,273 B2 | 11/2012 | Stellacci et al. |
| 8,500,979 B2 | 8/2013 | Elibol et al. |
| 8,557,567 B2 | 10/2013 | Park et al. |
| 8,617,966 B2 | 12/2013 | Wells |
| 8,691,608 B2 | 4/2014 | Harrer et al. |
| 8,882,980 B2 | 11/2014 | Ling et al. |
| 8,900,975 B2 | 12/2014 | Chang et al. |
| 9,012,329 B2 | 4/2015 | Astier |
| 9,013,010 B2 | 4/2015 | Chang et al. |
| 9,117,744 B2 | 8/2015 | Wells |
| 9,151,740 B2 | 10/2015 | Lee et al. |
| 9,194,838 B2 | 11/2015 | Taniguchi et al. |
| 9,274,430 B2 | 3/2016 | Gyarfas et al. |
| 9,290,806 B2 | 3/2016 | Stolovitzky et al. |
| 9,303,310 B2 | 4/2016 | Baldauf et al. |
| 9,354,195 B2 | 5/2016 | Tayebi et al. |
| 9,435,802 B2 | 9/2016 | Widdershoven |
| 9,494,554 B2 | 11/2016 | Davis et al. |
| 9,500,617 B2 | 11/2016 | Credo et al. |
| 9,506,894 B2 | 11/2016 | Kawai et al. |
| 9,535,033 B2 | 1/2017 | Kawai et al. |
| 9,630,175 B2 | 4/2017 | Naik et al. |
| 9,644,236 B2 | 5/2017 | Kawai et al. |
| 9,650,668 B2 | 5/2017 | Oliver et al. |
| 2004/0110277 A1 | 6/2004 | Maeda |
| 2010/0267158 A1 | 10/2010 | Chou et al. |
| 2012/0122715 A1* | 5/2012 | Gao ............... G01N 33/5438 506/9 |
| 2014/0031995 A1 | 1/2014 | Kawai et al. |
| 2014/0055150 A1 | 2/2014 | Kawai et al. |
| 2014/0190824 A1 | 7/2014 | Credo et al. |
| 2015/0014752 A1 | 1/2015 | D'emic et al. |
| 2015/0168341 A1* | 6/2015 | Tayebi ............... G01N 27/3278 204/403.01 |
| 2016/0138101 A1 | 5/2016 | Taniguchi et al. |
| 2016/0184819 A1* | 6/2016 | Naik ............... G01N 33/48721 216/17 |
| 2016/0187282 A1 | 6/2016 | Gardner et al. |
| 2016/0192504 A1 | 6/2016 | Eliobol et al. |
| 2016/0245789 A1 | 8/2016 | Ikeda et al. |
| 2016/0320364 A1 | 11/2016 | Ikeda et al. |
| 2016/0377591 A1 | 12/2016 | Kawai et al. |
| 2017/0122903 A1 | 5/2017 | Hu et al. |
| 2017/0131237 A1 | 5/2017 | Ikeda |
| 2017/0146510 A1 | 5/2017 | Ikeda et al. |

OTHER PUBLICATIONS

Yi et al., *Theoretical and Experimental Study Towards a Nanogap Dielectric Biosensor*, Biosensors & BioElectronics, © 2004 Elsevier, 7 pages.

Antonine, *Nanogap Sensor*, Memorandum, Aug. 24, 2017, 3 pages.

International Search Report and Written Opinion issued in International Patent Application Serial No. PCT/EP2018/077272 dated Apr. 3, 2019, 17 pages.

* cited by examiner

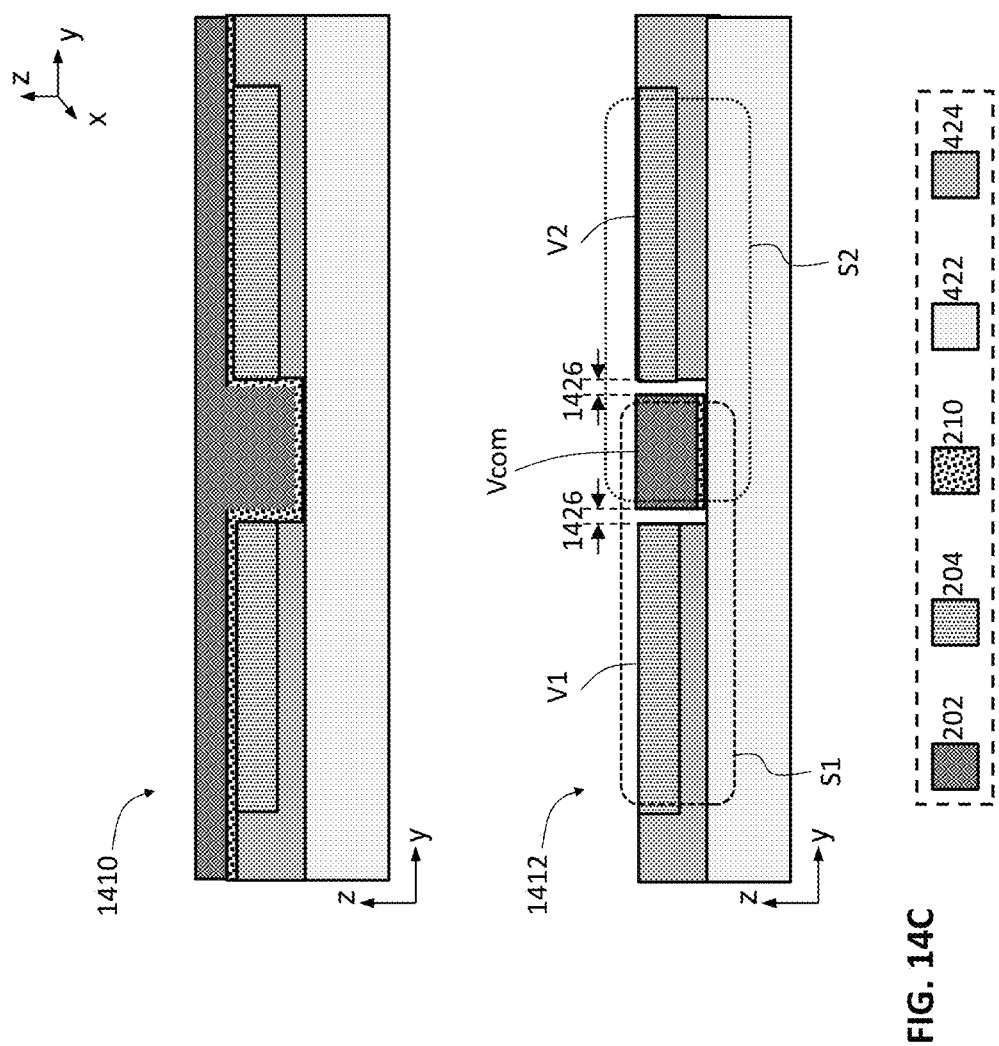

DESIGNS AND FABRICATION OF NANOGAP SENSORS

CROSS-REFERENCE TO RELATED APPLICATIONS

This application claims the benefit of and priority from U.S. Provisional Patent Application Ser. No. 62/571,921 filed 13 Oct. 2017, entitled "DESIGNS AND FABRICATION METHODS FOR NANOGAP SENSORS", incorporated herein by reference in its entirety.

TECHNICAL FIELD OF THE DISCLOSURE

The present invention relates to the field of sensors, in particular to sensors for evaluating analytes based on electron transfer or other transduction methods through a nanometric-sized gap between at least a pair of electrodes, and to methods of fabricating such sensors.

BACKGROUND

Evaluation of molecular content of various analytes is important in applications across a large variety of fields. For example, molecular identification may be used in deoxyribonucleic acid (DNA) or ribonucleic acid (RNA) sequencing used in biological research. In another example, identification of various gasses (e.g., $CO_2$, CO, $CH_4$, $H_2S$, etc.) or liquids (e.g., water) may be needed as some gasses or liquids may be dangerous for the environment or the living beings, as well as detrimental to the functionality or/and the efficiency of various devices such as e.g., integrated circuit (IC) chips.

Nanogap sensors may be used for evaluating molecular content of analytes. Designing and fabricating nanogap sensors is a non-trivial task because each application may have different needs in performance, cost and size. Improvements in nanogap sensor design and fabrication would enable to expand use of nanogap sensors.

BRIEF DESCRIPTION OF THE DRAWINGS

To provide a more complete understanding of the disclosure and features and advantages thereof, reference is made to the following description, taken in conjunction with the accompanying figures, wherein like reference numerals represent like parts, in which:

FIGS. 14A-14C illustrate example steps for fabricating a third vertical nanogap sensor, according to some embodiments of the disclosure;

Figure 2:
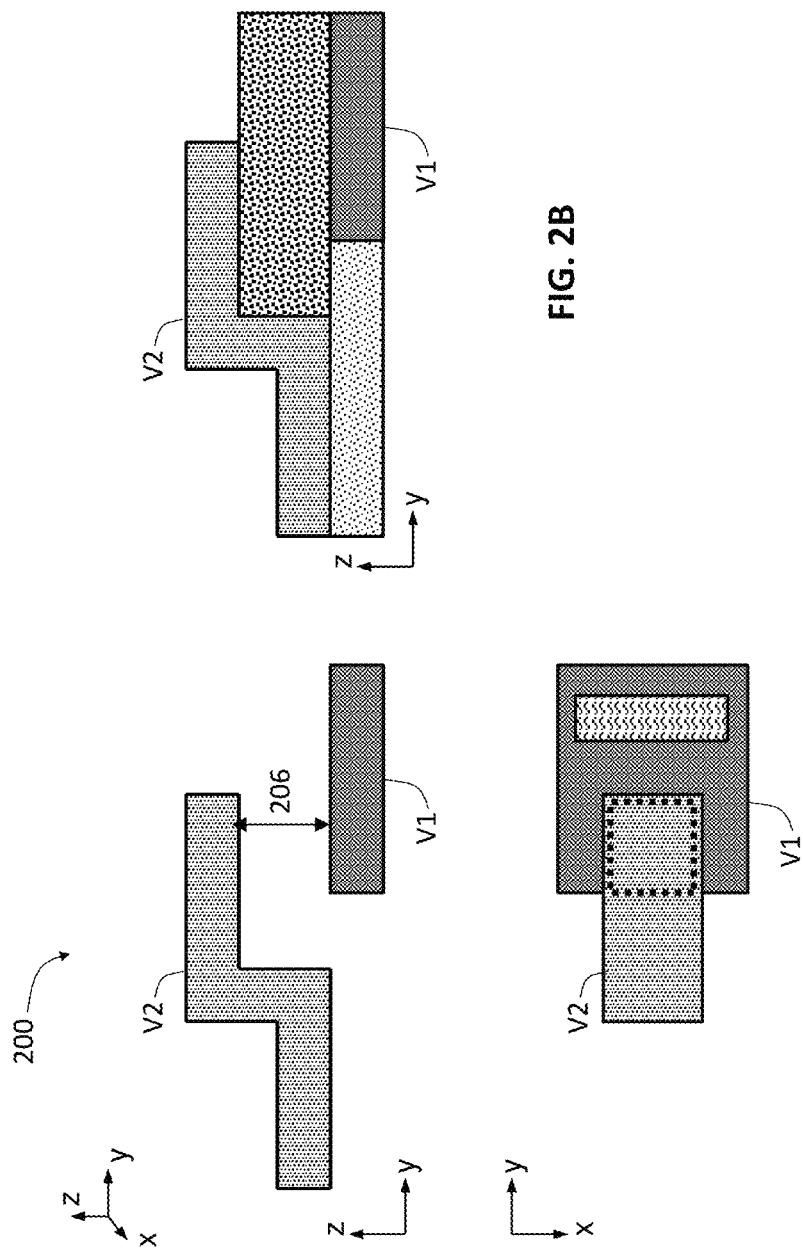
FIGS. 2A-2B illustrate an example fully-released cantilever nanogap sensor, according to some embodiments of the disclosure.

Some of the elements referred in the description of FIGS. with reference numerals are indicated in the FIGS. with different patterns, with a legend showing the correspondence between the reference numerals and patterns being provided at the bottom of each of such FIGS. within a box shown with a dashed line. For example, FIG. 2A uses different patterns to show an electrically conductive material 202 of a first electrode, an electrically conductive material 204 of a second electrode, a fluidic window 208, etc. Same or like reference numerals used in one of the FIGS. are intended to illustrate same or like elements in other FIGS., so that, unless stated otherwise, descriptions of these elements provided with respect to one of the FIGS. are to be assumed to be applicable to other FIGS. illustrating the same reference numerals, which descriptions are then not repeated in the interests of brevity.

DESCRIPTION OF EXAMPLE EMBODIMENTS OF THE DISCLOSURE

Overview

As mentioned above, nanogap sensors may be used for evaluating molecular content of analytes. In general, the term "nanogap sensor" refers to a device where at least two electrodes are separated by a nanometric-sized, tightly-confined region of space (i.e., a nanogap, also referred to as a "query volume") in which an analyte (i.e., a substance whose chemical constituents are being identified and/or measured) is provided. When voltage is applied to one or more of the electrodes, electrons can travel from a first electrode to a second electrode by tunneling. The molecules of the analyte present inside the nanogap affect electron tunneling. Therefore, readout of the current through the nanogap allows identification and evaluation of the molecular species within the nanogap. Other transduction methods such as impedance changes are also possible.

Embodiments of the disclosure provide various nanogap sensor designs (e.g., horizontal nanogap sensors, vertical nanogap sensors, arrays of multiple nanogap sensors, various arrangements for making electrical connections to the electrodes of nanogap sensors, etc.), as well as various methods which may be used to fabricate at least some of the proposed sensors. The nanogap sensors proposed herein may operate as molecular sensors in a broad sense, i.e., help identify chemical species through electrical measurements using at least a pair of electrodes separated by a nanogap. As used herein, the term "nanogap" refers to a cavity between a pair of electrodes such that the distance between the electrodes is on a nanometer scale. In various embodiments, such distance may be, e.g., between about 1 and 100 nanometers (nm), including all values and ranges therein, e.g., between about 2 and 50 nm, or between about 5 and 20 nm.

As used herein, description of any of the proposed nanogap sensors with reference to measuring chemical content of a target analyte assumes that, unless specified otherwise, a sensor can merely detect presence or absence of the target analyte, or may assess/evaluate/quantify the amount of the target analyte or various molecular components therein. Furthermore, while some nanogap sensors proposed herein may be described with reference to specific chemical (s) being an example target analyte of interest (such as e.g., DNA), these sensors are by no means limited to detecting presence and/or amount of such chemicals, and can easily be extended to measurements of other target analytes. In some implementations, the nanogap sensors proposed herein may be used for molecular measurements in a liquid phase (i.e., the analyte provided in the nanogap may be liquid), e.g., as used in DNA/RNA sequencing, reading of epigenetic markers, protein detection and identification, and various applications not related to life science, such as e.g., industrial chemical measurement. In other implementations, the nanogap sensors proposed herein may be used for molecular measurements in a gaseous phase (i.e., the analyte provided in the nanogap may be gaseous), e.g., as used in gas sensors or identification and quantification of chemical species in vehicles or buildings.

As will be appreciated by one skilled in the art, aspects of the disclosure, in particular aspects of nanogap sensor designs proposed herein, may be embodied in various manners—e.g., as systems used to carry out measurement of target analytes, methods used to fabricate said systems as well as methods used to operate said systems, computer program products comprising computer-readable instructions which, when executed on a processor, can operate said systems, or computer-readable storage media, preferably non-transitory, used to store such computer-readable instructions. Accordingly, aspects of the disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Some functions described in this disclosure may be implemented as algorithms executed by one or more processing units, e.g., one or more microprocessors, of one or more computers. The data obtained and/or results calculated by such a system may also be communicated using wired or wireless means appropriate to the application.

Other features and advantages of the disclosure will be apparent from the following description, and from the select examples.

The following detailed description of various embodiments of the disclosure is organized as follows. First, basics of DNA sequencing is described, followed by a description of an example nanogap sensor system with reference to FIG. 1. Next, various embodiments of horizontal nanogap sensors (i.e., nanogap sensors where a nanogap is horizontal in that one of the pair of electrodes is provided below the nanogap and the other one of the pair of electrodes is provided above the nanogap; in other words, the electrodes of a nanogap, as well as the nanogap itself, are provided parallel to the plane of the substrate/chip) are described with reference to FIGS. 2-8. After that, various embodiments of vertical nanogap sensors (i.e., nanogap sensors where a nanogap is vertical in that one of the pair of electrodes is provided on one side of the nanogap and the other one of the pair of electrodes is provided on the other side of the nanogap and both electrodes are provided perpendicular to the plane of the substrate/chip) are described with reference to FIGS. 9-15. Next, sharing of a common electrode for an array of horizontal nanogap sensors is described with reference to FIG. 16, and, finally a description of an example data processing system for carrying out molecular evaluation of a sample analyte using any of the nanogap sensors disclosed herein is provided with reference to FIG. 17.

In the following detailed description, various aspects of the illustrative implementations will be described using terms commonly employed by those skilled in the art to convey the substance of their work to others skilled in the art. For example, the terms "oxide," "carbide," "nitride," etc. refer to compounds containing, respectively, oxygen, carbon, nitrogen, etc. The terms "substantially," "close," "approximately," "near," and "about," generally refer to being within +/−20% of a target value described. While certain fabrication methods are described explicitly for some fabrication steps (e.g., describing particular deposition and patterning methods used to realize a fabrication step of providing a patterned element of an electrically conductive material, e.g., an electrode), when such methods are not explicitly mentioned for a certain step, it is to be assumed that conventional techniques or methods described elsewhere in the disclosure in context of a similar step may be used for realizing the step.

Basics of DNA Sequencing

In some implementations, the nanogap sensors and sensor arrays proposed herein may be used for DNA sequencing. In general, DNA sequencing may be performed by applying an electrical field to the DNA strand provided in a nanogap of a nanogap sensor, where the field is applied using electrodes of the nanogap sensor, and measuring the resulting tunneling current through the nanogap. Different base pairs will deliver different tunneling current characteristics (both current amplitude and time characteristics), which allows differentiation between these pairs.

An alternative approach to DNA sequencing may include attaching base pair labels biochemically and detecting the presence or absence of these labels on large arrays of nanogap sensors substantially simultaneously. Such an approach may be beneficial because it may provide an easier manner for discriminating between base pairs due to label selectivity and may advantageously result in various tunneling currents across the nanogaps which are easier to distinguish from one another.

While DNA sequencing techniques have been rapidly advancing in recent years, there are still challenges to overcome, such as e.g., processing very large numbers of base reads in parallel, discriminating between pairs, getting reproducible reads from a given strand independent of the sensor variations, performing measurements sufficiently quickly, and dealing with read errors. Therefore, new and improved nanogap sensors and arrays of such sensors are needed.

Example Nanogap Sensor System

Figure 1:
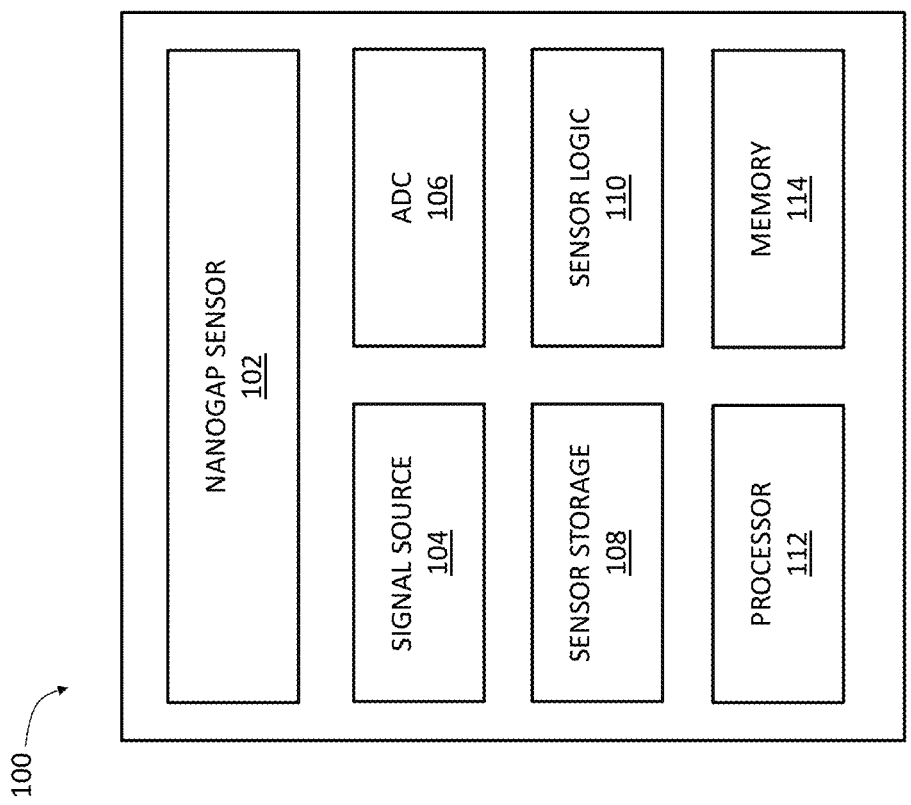
FIG. 1 illustrates an example nanogap sensor system, according to some embodiments of the disclosure.

FIG. 1 illustrates an example nanogap sensor system 100, according to some embodiments of the disclosure. As shown in FIG. 1, the example system 100 may include one or more nanogap sensors 102. Oftentimes, including multiple nanogap sensors 102, e.g., hundreds, thousands, or even millions of nanogap sensors 102, may be desirable as it may improve throughput and accuracy by parallel operation of multiple sensors on a given chip. Each of the nanogap sensors 102 may be any of the nanogap sensors proposed herein, and a plurality of the nanogap sensors 102 may be arranged according to any of the arrangements of proposed nanogap sensors described herein.

As briefly described above, each nanogap sensor includes at least a pair of electrodes to which signals are applied in order to evaluate the chemical species in the nanogap. In some embodiments, using more than two electrode for a given query volume (i.e., for what may be considered a single nanogap sensor) may be beneficial as it may allow for more measurements of current tunneled through the query volume and may highlight more detailed characteristics of the species in the query volume, e.g., different pairs of electrodes may be used to query the volume along various spatial directions. Hence, unless stated otherwise, for each of the nanogap sensors proposed herein, even though two electrodes may be described, the descriptions may be extended to more than two electrodes, all of which descriptions being within the scope of the disclosure.

In some instances, a carrier molecule in the fluid inside the nanogap can exchange with a first electrode charges such as electrons for example, then travel to a second electrode and exchange charges there. This step where a molecular carrier acts as a charge transporter across a nanogap is used in so-called "redox cycling" techniques. In other instances, a conductor-molecule-conductor junction can be formed between the two conducting electrodes and across the nanogap such as electron transport across the nanogap is changed by the presence of this newly-formed molecular bridge.

For all embodiments of the nanogap sensors described herein, in some embodiments, one or more layers of specifically designed molecules/compounds may be provided on at least portions of surfaces of either one or both of the pair of electrodes that face one another. Such layers may promote attachment or coupling of analytes to be evaluated, which may be advantageous for certain tests to be carried out using the nanogap sensor system. In some embodiments, such one or more layers may be self-assembled monolayer (SAMs), and may include one or more of thiols (R-S-H), dithiols (H-S-R-S-H), or alkanethiols (e.g., mercapto-propanol or mercaptohexanol).

As shown in FIG. 1, the nanogap sensor system 100 may include a signal source 104 for applying appropriate signals to the electrodes of the one or more nanogap sensors 102.

The signal source 104 may be configured to apply various signal waveforms to each electrode pair as "query waveforms."

As further shown in FIG. 1, the nanogap sensor system 100 may also include one or more analog to digital converters (ADCs) 106. In general, ADCs are electronic devices that convert a continuous physical quantity carried by an analog signal to a digital number that represents the quantity's amplitude (or to a digital signal carrying that digital number). The conversion involves quantization of the analog input signal. Typically the quantization occurs through periodic sampling of the analog input signal. The result is a sequence of digital values (i.e., a digital signal) that has converted a continuous-time and continuous-amplitude analog input signal to a discrete-time and discrete-amplitude digital signal. In case of the ADC 106 used in the nanogap sensor system 100, the analog input signal being converted may be signal indicative of the electrical current across the nanogap(s) of the one or more nanogap sensors 102.

There are many types of ADC technologies such as flash, sigma-delta, SAR converters, etc., and these different styles of converters may be used in combination to implement the one or more ADCs 106. In some implementations of the one or more ADCs 106, an input signal may be sampled onto a capacitor or an array of capacitors commonly referred to as "sampling capacitors" prior to the analog to digital conversion taking place. During the sampling operation, charge is exchanged between the sampling capacitor(s) and a circuit driving the sampling capacitor(s) so that the sampling capacitor(s) are charged to a voltage corresponding to the value of the input signal at that time. The driving circuit typically has an impedance such that it takes time to charge and discharge the sampling capacitor to its correct voltage. Terms such as "acquisition/acquire phase" or "sampling phase" may be used to describe a phase, i.e., a time period, when sampling capacitor(s) connected to an input node at which the input signal is received are being charged to a voltage corresponding to the input voltage. In other words, "acquire phase" or "sampling phase" refer to a time period when sampling capacitor(s) are sampling an analog input signal in order to convert the analog input signal to a digital output signal. Terms "sampling" and "acquire phase" may be used interchangeably to refer to the action of one or more sampling capacitors connected to an input node sampling or acquiring an input signal during a certain time period. An acquire phase is followed, which may but does not have to be in immediate succession (i.e., may or may not be done consecutively), by a phase that is typically referred to as a "conversion phase," where an analog value of the input signal sampled on the sampling capacitor(s) is converted to a digital value by comparison of the charge accumulated on the sampling capacitor(s) with one or more reference voltage values. After acquisition and conversion phases for converting one analog input value are finished, processing described above is repeated for the next analog input value.

In other implementations of the one or more ADCs 106, an analog input signal may be converted into a digital form using a relaxation oscillator configured to oscillate with an oscillation frequency indicative of the input signal. Since the input signal is indicative of the current generated by one of the nanogap sensors 102, the oscillation frequency of the relaxation oscillator would also be indicative of the current generated by that nanogap sensor.

In some embodiments, the relaxation oscillator may be a relatively simple current-controlled relaxation oscillator per channel, which, when coupled with a counter (not specifically shown in figures) may convert the analog input current into a digital value. In such an oscillator, the input current signal may be transformed, by the relaxation oscillator, into increasing phase of the oscillator, quantized to output "cycles." The cycles are counted by the counter to accumulate the digitized input signal over a given measurement interval. Such an approach to converting the current generated by a nanogap sensor from analog to digital domain may advantageously reduce or eliminate the need for large sampling capacitors and/or attenuation of said current, which might need to be used with other conversion approaches. Thus, using such a relaxation oscillator may advantageously enable use of only a relatively small capacitor in the oscillator itself (i.e., no integration of the analog input is performed on the capacitor(s), instead the integration of the input may be performed through digital accumulation in the counter).

In particular, the phase of a relaxation oscillator may represent the integral of the input current, i.e., the charge indicative of the input current from the nanogap sensor being readout. In the digital output from the relaxation oscillator this phase becomes quantized to integer cycles. Then, by accumulating the total number of cycles in the counter, the input signal is integrated throughout the measurement interval. Thus, using a relaxation oscillator in such a readout scheme allows, first, digitizing the input current, and then integrating the result in digital form, i.e., this approach may be referred to as a "first digitize then integrate" approach. This is fundamentally different from alternative readout schemes in which the input current from the nanogap sensors is first integrated in analog form using sampling capacitors, and is digitized after the integration, i.e., an approach which may be referred to a "first integrate then digitize" approach (i.e., first, integrating all the signal for a given measurement, and then only afterwards digitizing with a high-dynamic-range ADC).

An ADC is usually defined by the following operating characteristics, typically provided as part of application requirements: its bandwidth (the range of frequencies of analog signals that can be properly converted to a digital signal), its resolution (the number of discrete levels that the maximum analog signal can be divided into and represented in the digital signal), its signal to noise (SNR) ratio (how accurately the ADC can measure signal relative to the noise the ADC introduces), and its dynamic range (the minimum resolvable step size and the ratio between the largest and smallest possible inputs). ADCs 106 have many different designs, which can be chosen based on the operating characteristics required by different applications.

Turning back to FIG. 1, the sensor readings corresponding to currents through the nanogaps of the one or more nanogap sensors 102 may be stored in a sensor storage 108, which may be any suitable array of memory elements. In some embodiments, the sensor storage 108 may include an array of capacitors, where voltage on each capacitor is indicative of the current though a nanogap of a particular nanogap sensor 102, possibly for a particular arrangement of a pair of electrodes around such a gap (e.g., in case multiple pairs of electrodes are used for a single nanogap).

As also shown in FIG. 1, the nanogap sensor system 100 may further include nanogap sensor logic 110, which may be implemented in hardware, software, firmware, or any suitable combination of one or more of these, is configured to control the implementation and operation of the nanogap sensors in the nanogap sensor system 100 as described herein. To that end, the nanogap sensor logic 110 may make use of at least one processor 112 and at least one memory element 114, along with any other suitable hardware and/or software to enable its intended functionality of nanogap sensor readings in a nanogap sensor system as described herein. In some embodiments, the processor 112 can execute software or an algorithm to perform the activities as discussed in the disclosure, e.g., the processor 112 can execute the algorithms that carry evaluation of input analog values to measure the chemical species present within the nanogaps of the one or more nanogap sensors 102 as described herein. Although shown as separate elements in FIG. 1, the processor 112 and/or the memory 114 may be considered to be a part of the nanogap sensor logic 110.

The processor 112 may be configured to communicatively couple to other system elements via one or more interconnects or buses. Such a processor may include any combination of hardware, software, or firmware providing programmable logic, including by way of non-limiting example a microprocessor, a digital signal processor (DSP), a field-programmable gate array (FPGA), a programmable logic array (PLA), an application specific IC (ASIC), or a virtual machine processor. The processor 112 may be communicatively coupled to the memory element 114, for example in a direct-memory access (DMA) configuration. Such a memory element may include any suitable volatile or non-volatile memory technology, including double data rate (DDR) random access memory (RAM), synchronous RAM (SRAM), dynamic RAM (DRAM), flash, read-only memory (ROM), optical media, virtual memory regions, magnetic or tape memory, or any other suitable technology. Unless specified otherwise, any of the memory items discussed herein should be construed as being encompassed within the broad term "memory element." The information being tracked or sent to the one or more nanogap sensors 102, the signal source 104, the ADC 106, the sensor storage 108, the nanogap sensor logic 110, the processor 112, or the memory 114 could be provided in any database, register, control list, cache, or storage structure, all of which can be referenced at any suitable timeframe. Any such storage options may be included within the broad term "memory element" as used herein. Similarly, any of the potential processing elements, modules, and machines described herein should be construed as being encompassed within the broad term "processor." Each of the elements shown in FIG. 1, e.g., the nanogap sensor logic 110 and the AC 106, can also include suitable interfaces for receiving, transmitting, and/or otherwise communicating data or information in a network environment.

In certain example implementations, mechanisms for evaluating molecular content of analytes based on electrical readings across nanogaps in nanogap sensor systems as outlined herein may be implemented by logic encoded in one or more tangible media, which may be inclusive of non-transitory media, e.g., embedded logic provided in an ASIC, in DSP instructions, software (potentially inclusive of object code and source code) to be executed by a processor, or other similar machine, etc. In some of these instances, memory elements, such as e.g., the memory 114 shown in FIG. 1, can store data or information used for the operations described herein. This includes the memory elements being able to store software, logic, code, or processor instructions that are executed to carry out the activities described herein. A processor can execute any type of instructions associated with the data or information to achieve the operations detailed herein. In one example, the processors, such as e.g., the processor 112 shown in FIG. 1, could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., an FPGA, a DSP, an erasable programmable read-only memory (EPROM), an electrically erasable programmable read-only memory (EEPROM)) or an ASIC that includes digital logic, software, code, electronic instructions, or any suitable combination thereof.

Horizontal Nanogap Sensor Designs

Horizontal nanogap sensors described herein may be viewed as variations of an idea of the beam with the top electrode being provided above the bottom electrode with a nanometric horizontal gap in between, i.e., the nanogap is a gap region provided in a plane parallel to the plane of the wafer/chip/substrate.

FIG. 2A illustrates a first horizontal nanogap sensor 200, in particular, an example fully-released cantilever nanogap sensor, according to some embodiments of the disclosure. As used herein, the term "fully-released cantilever" is used to describe structures with a substantially complete sacrificial release so that one electrode is not connected to another electrode with a sacrificial material. In contrast, the term "partially-released cantilever" is used to describe structures where the sacrificial release is not complete in that one electrode may still be connected to another electrode with a sacrificial material.

As shown in FIG. 2A, the horizontal nanogap sensor 200 may have a first electrode V1 made of an electrically conductive material 202, and a second electrode V2 made of an electrically conductive material 204 and provided over and overlapping with the first electrode V1, while being separated from the first electrode V1 by a nanogap 206. The second electrode V2 is provided as a projecting beam or girder fixed at only one end (namely, the portion shown on the left side of FIG. 2A), thus justifying the term "cantilever" used to describe this design. While FIG. 2A illustrates that the second electrode V2 is shorter than the first electrode V1, in various embodiments, the second electrode V2 may be longer than or extend to be of the same length as the first electrode V1.

In various implementations, the electrically conductive materials 204 and 206 may be the same or different materials. In various embodiments, each of the electrically conductive materials 204 and 206 may include any suitable electrically conductive material typically used in semiconductor manufacturing, such as e.g., any metal or metal alloys, e.g., one or more of platinum, gold, copper, nickel, aluminum, titanium, etc.

The upper view of the nanogap sensor 200 provided in FIG. 2A is a side view cross-section, while the lower view of the nanogap sensor 200 provided in FIG. 2A is a top view. The top view shown in FIG. 2A schematically illustrates a location of a fluidic window 208, which may be a window in a material encapsulating the first and second electrodes of the nanogap sensor 200 (such material not specifically shown in FIG. 2A), which window would allow the fluidic analytes (i.e., analytes in liquid of gaseous states) to be provided within the nanogap 206 in order for the measurements characterizing these analytes can be performed.

In various embodiments, the thickness of the nanogap 206 (i.e., a dimension measured along the z axis of the x-y-z coordinate system shown in FIG. 2A) may be between about 1 and 100 nm, including all values and ranges therein, e.g., between about 5 and 50 nm, or between about 5 and 20 nm. In various embodiments, the second electrode V2 may overlap with the first electrode V1 an area indicated in the bottom view of FIG. 2A with a dotted contour, which area could be between about 1,000 and 100,000,000 nm2, including all values and ranges therein, e.g., between about 2,500 and 50,000,000 nm2, or between about 5,000 and 20,000,000 nm2.

FIG. 2B provides a view of the horizontal nanogap sensor 200 substantially as shown in the upper view of the nanogap sensor 200 provided in FIG. 2A, further showing a sacrificial material 210 being used in order to form the nanogap 206, as described in greater detail below, as well as showing a material 212 on which the second electrode V2 can be provided.

The sacrificial material 210 is referred to as "sacrificial" because, during the fabrication of the horizontal nanogap sensor 200 some or all of the material may be removed, e.g., by any suitable etching technique, resulting in creation of the nanogap 206. Thus, the sacrificial material 210 is to be selected as having suitable etching characteristics with respect to the materials of the surrounding elements, in particular with respect to the first and second electrodes V1, V2, so that the etching of the sacrificial material 210 does not result in etching of these surrounding elements, or, at least, so that the etching of the sacrificial material 210 takes place much faster as the etching of the surrounding elements so that, when the etch process is over, the surrounding elements are not substantially etched. In other words, the sacrificial material 210 is a material that is sufficiently etch selective with respect to the materials of the surrounding elements. In various embodiments, the sacrificial material 210 may include any of the known materials conventionally used in semiconductor fabrication, such as e.g., silicon nitride (SiN), silicon oxide, silicon oxynitride, etc.

The material 212 may include dielectric materials such as silicon dioxide, silicon nitride, silicon oxynitride, aluminum oxide, tantalum oxide, etc., polymer materials such as photoresist, polyimide, PTFE or similar, or conductive materials such as titanium, titanium tungsten, chromium etc. In the case of the conductive sacrificial layers these are often combined with the electrode metal (e.g., TiW/Au) and deposited as a stack.

Figure 3:
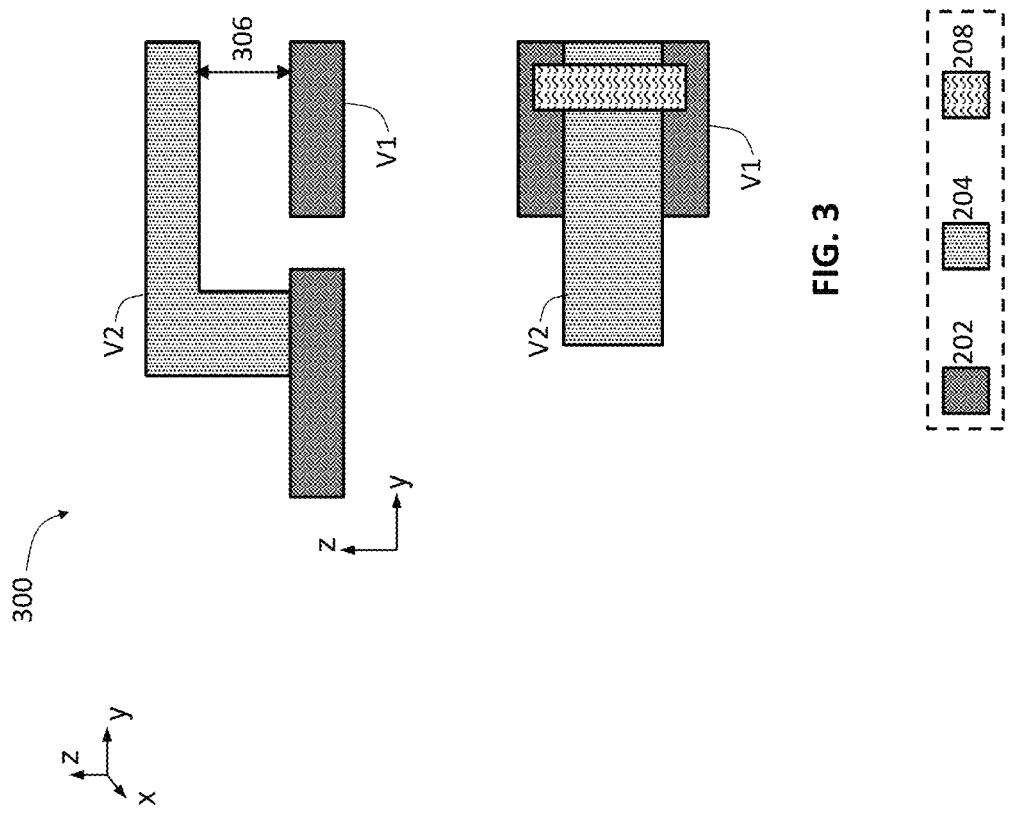
FIG. 3 illustrates an example fully-released cantilever nanogap sensor, according to other embodiments of the disclosure.

FIG. 3 illustrates a second horizontal nanogap sensor 300, in particular, an example fully-released cantilever nanogap sensor different from that shown in FIGS. 2A-2B, according to some embodiments of the disclosure. Similar to the nanogap sensor 200, the nanogap sensor 300 includes the first electrode V1 and the second electrode V2 made of the electrically conductive materials 202 and 204 as described above and separated by a nanogap 306 which could be substantially similar to the nanogap 206 described above. In contrast to the nanogap sensor 200, a lead contact to the second electrode V2 of the nanogap sensor 300 is made of the electrically conductive material 202 used to make the first electrode V1. Such implementation may be particularly advantageous because the metal pad 202 can be used to securely anchor the top electrode V2, 204 as well as providing the V1 electrode and providing a more planar surface on which to fabricate the top electrode V2.

Any of the nanogap sensors described herein may be fabricated using any suitable fabrication methods, examples of some of which are proposed herein. For example, FIG. 4 illustrates example steps for fabricating a fully-released cantilever nanogap sensor such as the one shown in FIG. 3, according to some embodiments of the disclosure.

Figure 4:
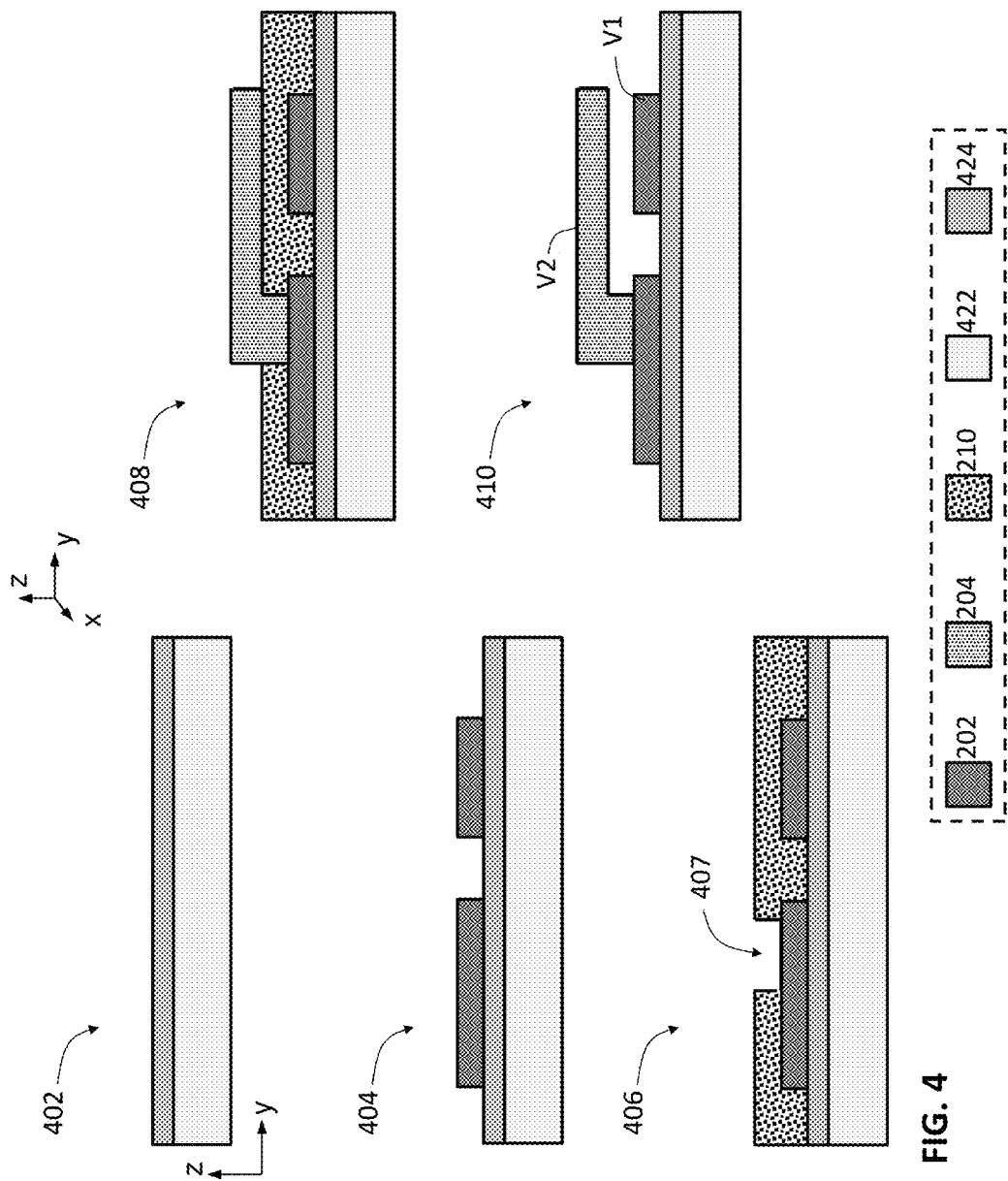
FIG. 4 illustrates example steps for fabricating a fully-released cantilever nanogap sensor, according to some embodiments of the disclosure.
Figure 5:
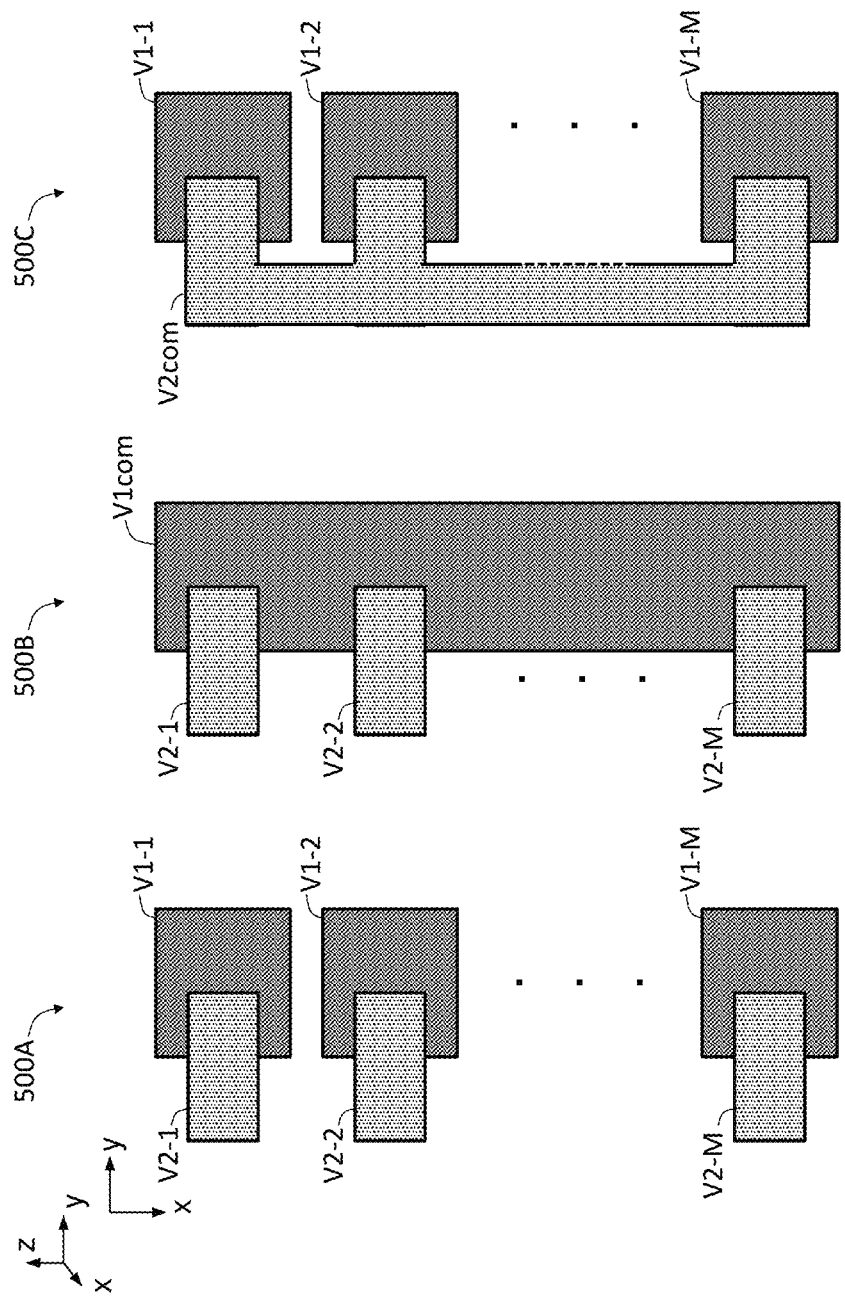
FIGS. 5A-5C illustrate example arrays of fully-released cantilever nanogap sensors, according to various embodiments of the disclosure.

Turning to FIG. 4, the method may begin starting with a substrate 422, which could be any of semiconductor substrates conventionally used in semiconductor manufacturing, such as e.g., a silicon substrate, which may, optionally, include a layer of an insulating material over it, e.g., a layer of a silicon oxide 424, as shown with a structure 402 illustrated in FIG. 4.

Next, a layer of the electrically conductive material 202 may be provided over the surface of the structure 402, and patterned as shown in FIG. 4 with a structure 404. Any suitable deposition and patterning techniques may be used to provide patterned elements of the electrically conductive material 202. Examples of deposition techniques used for depositing electrically conductive materials such as the material 202, as well as other electrically conductive materials/elements described herein, include atomic layer deposition (ALD) or physical vapor deposition (PVD) such as e.g., sputtering, or any combination thereof. Examples of patterning techniques used for patterning various (not necessarily electrically conductive) materials such as the material 202, as well as other materials/elements described herein include photolithographic patterning, electron-beam patterning, mask-patterning, or any combination thereof. In some embodiments, the electrically conductive material 202 used in the structure 404 may be platinum (Pt) or gold (Au).

A thin layer of the sacrificial material 210 may then be provided over the patterned first conductive material of the structure 404 and patterned so that a window/opening 407 is formed over one patterned element of the first conductive material 202, which will allow for making an electrical connection from that patterned element to the future second electrode V2, as shown in FIG. 4 with a structure 406. The sacrificial material 210 may be any of the materials as described above. Various deposition and patterning technique as known in the art may be used to deposit and pattern the sacrificial material 210, such as e.g., deposition by ALD, PVD, chemical vapor deposition (CVD), spin-coating, or dip-coating, possibly in combination with patterning such as e.g., photolithographic or electron-beam patterning. In various embodiments, a thickness of the sacrificial material above the patterned first conductive material of the structure 404 (i.e., a dimension measured along the z axis of the x-y-z coordinate system shown in FIG. 4) may be between about 1 and 100 nm, including all values and ranges therein, e.g., between about 2 and 50 nm, or between about 2 and 20 nm. In some embodiments, the sacrificial material 210 used in the structure 406 may be silicon oxide or silicon nitride.

Next, the electrically conductive material 204 is deposited over the structure 406 and patterned as shown in FIG. 4 with a structure 408. To that end, any suitable deposition and patterning techniques may be used, such as e.g., those described above with reference to the electrically conductive material 202. As a result of depositing the electrically conductive material 204 over the structure 406, the electrically conductive material 204 is provided within the opening 407, thus making electrical connection to the electrically conductive material 202 exposed by the opening 407. In some embodiments, the electrically conductive material 204 used in the structure 408 may be gold (Au).

Fabrication of the nanogap sensor may conclude with removing the sacrificial material 210 in order to fully release the second electrode V2 from the first electrode V1, the result of which is shown in FIG. 4 with a structure 410 showing electrodes V2 and V1 of a nanogap sensor such as the horizontal nanogap sensor 300 shown in FIG. 3. In various embodiments, any suitable etching techniques, such as e.g., wet etch or dry etch, using any suitable etchants, may be used to remove the sacrificial material 210. Various etching techniques are known in the art, all of which are within the scope of the disclosure. In some embodiments, dilute etch of phosphoric, acetic, and nitric acids (commonly referred to as "PAN etch") may be used to remove the sacrificial material 210.

While the structure 410 shown in FIG. 4, as well as the nanogap sensor 300 shown in FIG. 3, illustrate that the second electrode V2 (i.e., the cantilever electrode) extends over the first electrode V1 to be substantially aligned with the first electrode V1, in various other embodiments, the second electrode V2 may be longer or shorter than the first electrode V1.

In various embodiments, nanogap sensors as proposed herein may be arranged in arrays formed of individual sensors (i.e., no shared electrodes), or arrays formed of sensors at least some of which share electrodes. FIGS. 5A-5C illustrate example arrays of fully-released cantilever nanogap sensors, according to various embodiments of the disclosure. Each of FIGS. 5A-5C illustrates a top view, i.e., a view in the plane x-y of the coordinate system shown in the present FIGS.

In particular, FIG. 5A illustrates an array 500A of individual (i.e., no shared electrodes) cantilever nanogap sensors, each of which could be any of the fully-released horizontal nanogap sensors described above. FIG. 5A illustrates M such nanogap sensors (where M is an integer greater than 1), pairs of electrodes for which are denoted as a pair of a first electrode V1-1 and a second electrode V2-1 for a first sensor, a pair of a first electrode V1-2 and a second electrode V2-2 for a second sensor and so on, until a pair of a first electrode V1-M and a second electrode V2-M for an Mth sensor.

Figure 7A:
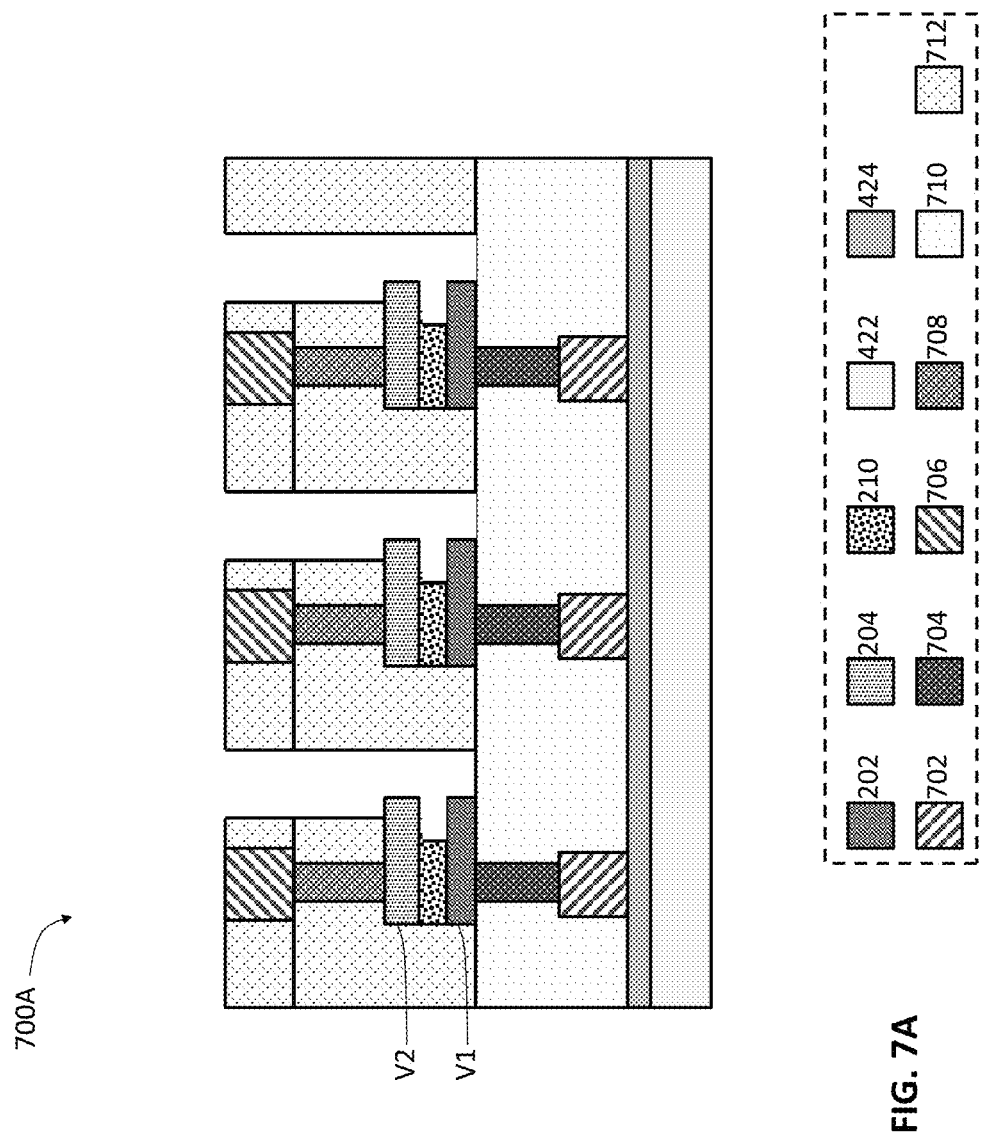
FIGS. 7A-7B illustrate different assemblies integrating one or more cantilever nanogap sensors, according to various embodiments of the disclosure.
Figure 7B:
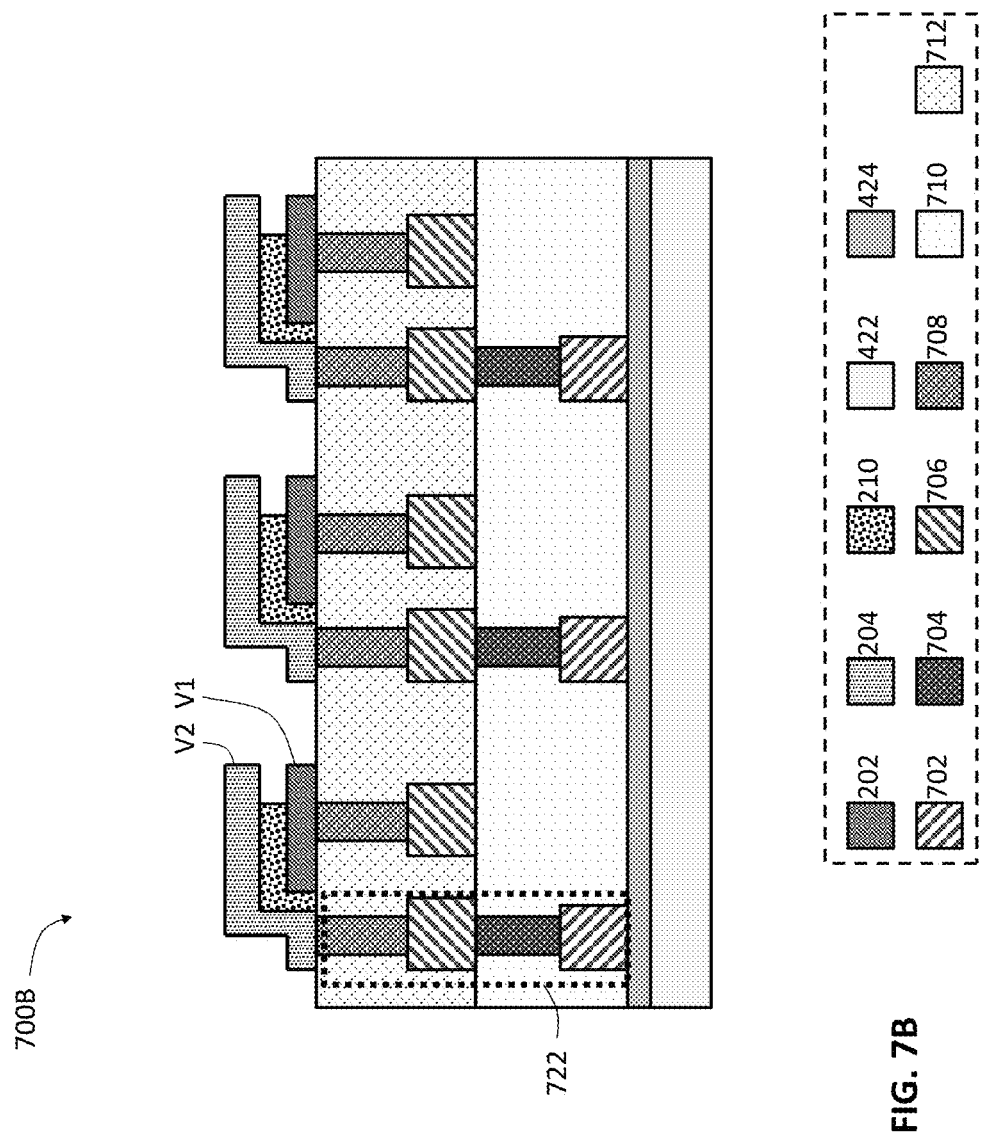

FIGS. 5B and 5C illustrate how one of the pair of electrodes for one or more of the nanogap sensors may be shared with another one or more of the nanogap sensors. In particular, FIG. 5B illustrates an array 500B of cantilever nanogap sensors, each of which could be any of the fully-released horizontal nanogap sensors described above, sharing a base electrode (i.e., sharing the first electrode V1). FIG. 5B illustrates M such nanogap sensors (where M is an integer greater than 1), where a shared first electrode for these sensors is denoted as a common first electrode V1com, while individual second electrodes for each one of the sensors are denoted as a second electrode V2-1 for a first sensor, a second electrode V2-2 for a second sensor and so on, until a second electrode V2-M for an Mth sensor. On the other hand, FIG. 5C illustrates an array 500C of cantilever nanogap sensors, each of which could be any of the fully-released horizontal nanogap sensors described above, sharing a cantilever electrode (i.e., sharing the second electrode V2). FIG. 5C illustrates M such nanogap sensors (where M is an integer greater than 1), where a shared second electrode for these sensors is denoted as a common second electrode V2com, while individual first electrodes for each one of the sensors are denoted as a first electrode V1-1 for a first sensor, a first electrode V1-2 for a second sensor and so on, until a first electrode V1-M for an Mth sensor. Sharing of a single electrode among multiple nanogap sensors may be advantageous in terms of saving space on the chip implementing such nanogap sensors. In addition, it may allow reducing the overall area (i.e., "real-estate" on the wafer) overhead due to the mask misalignment tolerance requirements. Additional layers of interconnect wiring will be needed to complete the integrated system. Such schemes are illustrated in FIG. 7A and FIG. 7B.

Figure 6:
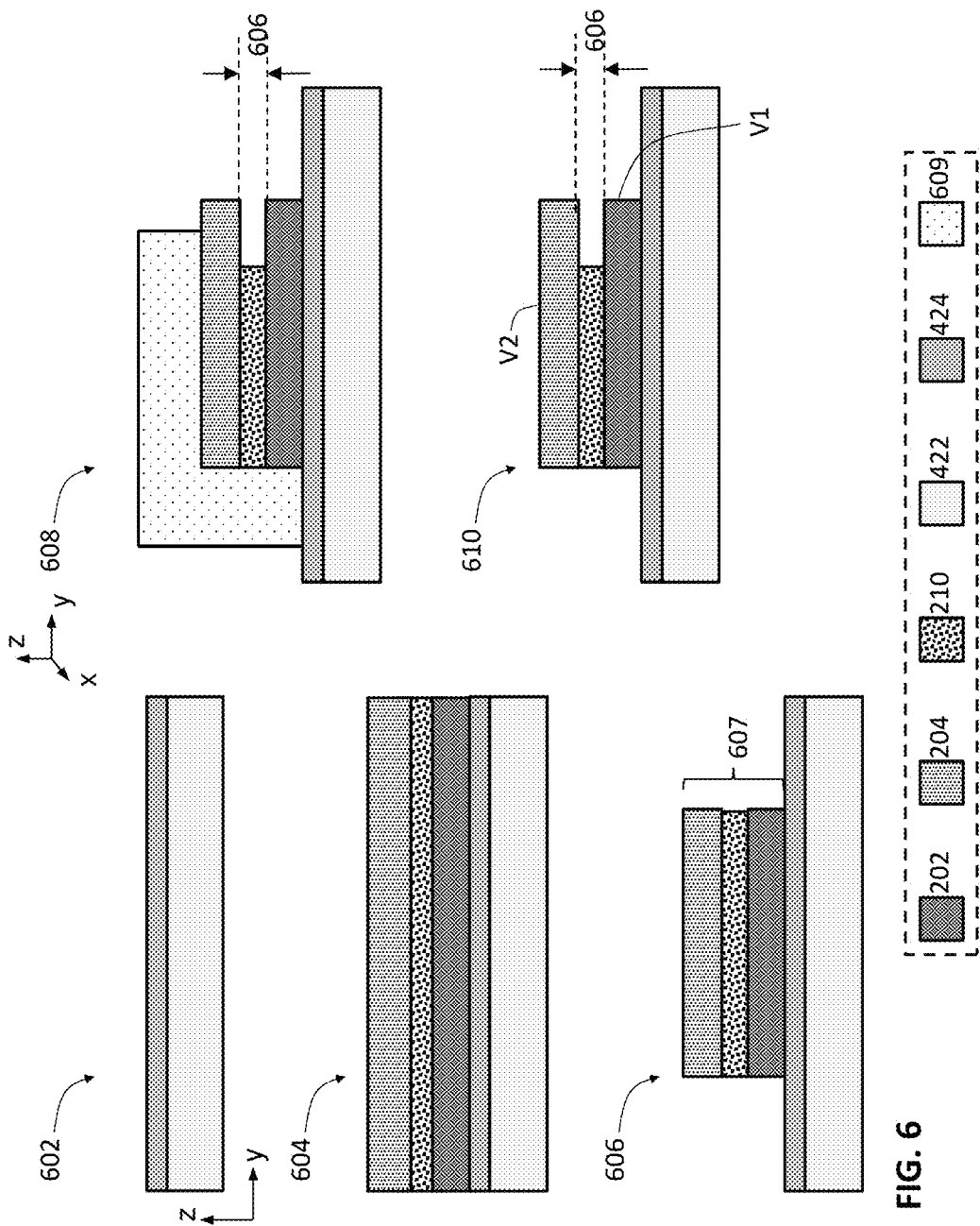
FIG. 6 illustrates example steps for fabricating a partially-released cantilever nanogap sensor, according to some embodiments of the disclosure.

While horizontal nanogap sensors described above are examples of fully-released horizontal nanogap sensors, FIG. 6 illustrates example steps for fabricating a partially-released cantilever nanogap sensor, according to some embodiments of the disclosure.

The method of FIG. 6 may begin starting with a substrate 422 as described above, which may, optionally, include a layer of an insulating material over it, e.g., a layer of a silicon oxide 424 as described above, as shown with a structure 602 illustrated in FIG. 6.

Next, layers of the electrically conductive material 202, the sacrificial material 210, and the electrically conductive material 204, as described above, may be provided over the surface of the structure 602, as shown in FIG. 6 with a structure 604. In some embodiments, each of the electrically conductive materials 202 and 204 may include Pt, and the sacrificial material 210 may include SiN. Any of the deposition techniques as known in the art may be used to deposit the layers of the structure 604, e.g., any of the deposition techniques described above.

Next, layers of the electrically conductive material 202, the sacrificial material 210, and the electrically conductive material 204 of the structure 604 may be patterned as shown in FIG. 6 with a structure 606 illustrating that a stack 607 is defined. In some embodiments, each of the electrically conductive materials 202 and 204 may include Pt, and the sacrificial material 210 may include SiN. Any of the deposition techniques as known in the art may be used to deposit the layers of the structure 604, e.g., any of the deposition techniques described above.

The method may further include a step of providing a mask 609 over a portion of the stack 607 of the structure 606 that would allow etching of the sacrificial material 210 within the stack 607 on one side of the stack, as shown in FIG. 6 with a structure 608. As a result of the etch, a nanogap 606 may be formed between the first electrode V1 and the second electrode V2, which could have dimensions similar to those described above with reference to the nanogap 206. Thus, an undercut is created in the sacrificial material 210, which undercut results in the formation of the desired nanogap 606. The sacrificial material 210 may only be etched partially, so that some of the sacrificial material 210 may remain between the first and second electrodes V1 and V2. To that end, a timed etch, e.g., a timed wet etch, may be used to partially etch the sacrificial material 210.

After the partial etch of the sacrificial material 210, the mask 609 may be removed, resulting in a partially-released horizontal nanogap sensor as shown with a structure 610 in FIG. 6.

In various embodiments, multiple partially-released horizontal nanogap sensors such as the one shown in the structure 610 of FIG. 6 may be arranged in arrays, e.g., in arrays similar to those described above with reference to FIGS. 5A-5C, all of which arrangements are within the scope of the disclosure.

Cantilever nanogap sensors as described herein may be integrated with metallization layers in various manners. FIGS. 7A-7B illustrate different assemblies integrating one or more cantilever nanogap sensors, according to various embodiments of the disclosure, using the partially-released cantilever nanogap sensor as shown in the structure 610 of FIG. 6 as an example. FIGS. 7A and 7B differ in how a connection to the top electrode V2 (i.e., the second, or cantilever, electrode) is provided. Namely, FIG. 7A illustrates connection to the top electrode using a metallization stack above the nanogap, while FIG. 7B illustrates connection to the top electrode using a metallization stack below the nanogap. Each of FIGS. 7A-7B illustrates an array with 3 nanogap sensors, but in other embodiments, any other number of one or more of such nanogap sensors may be used. Furthermore, based on the descriptions provided herein with respect to connecting to the electrodes of a partially-released cantilever nanogap sensors illustrated in FIGS. 7A-7B, similar connections can be provided for fully-released cantilever nanogap sensors as described herein, all of which embodiments being, therefore, within the scope of the disclosure.

FIG. 7A illustrates an embodiment of an assembly 700A where, for each of a pair of electrodes V1 and V2 for a given horizontal nanogap sensor, the first electrode V1 is connected to an element of a first metallization layer (M1) 702, e.g., using a first via 704, while the second first electrode V2 is connected to an element of a second metallization layer (M2) 706, e.g., using a second via 708. FIG. 7A illustrates that the metallization layer 702 and the first vias 704 may be provided within a material 710, while the metallization layer 706 and the second vias 708 may be provided within a material 712. Each of the materials 710 and 712 could include a suitable insulating dielectric material in order to electrically separate various electrically conductive elements from one another, e.g., any of the conventional interlayer dielectric layer (ILD) materials used in semiconductor processing. In various embodiments, the ILD materials 710 and 712 could be the same or different materials. Various materials/elements shown in FIG. 7A using reference numerals as described above are intended to show similar or analogous elements, which descriptions, therefore, are not repeated here in the interests of brevity.

FIG. 7B illustrates an embodiment of an assembly 700B where, for each of a pair of electrodes V1 and V2 for a given horizontal nanogap sensor, the first electrode V1 is connected to an element of the second metallization layer (M2) 706, e.g., using the second via 708, while the second electrode V2 is connected to an element of the first metallization layer (M1) 702, e.g., using the first via 704 in combination with an associated second via 708 and the associated element of the second metallization layer M2 706. The connection for the second electrode V2 is indicated in FIG. 7B with a dotted contour and labeled as a connection 722.

Figure 8:
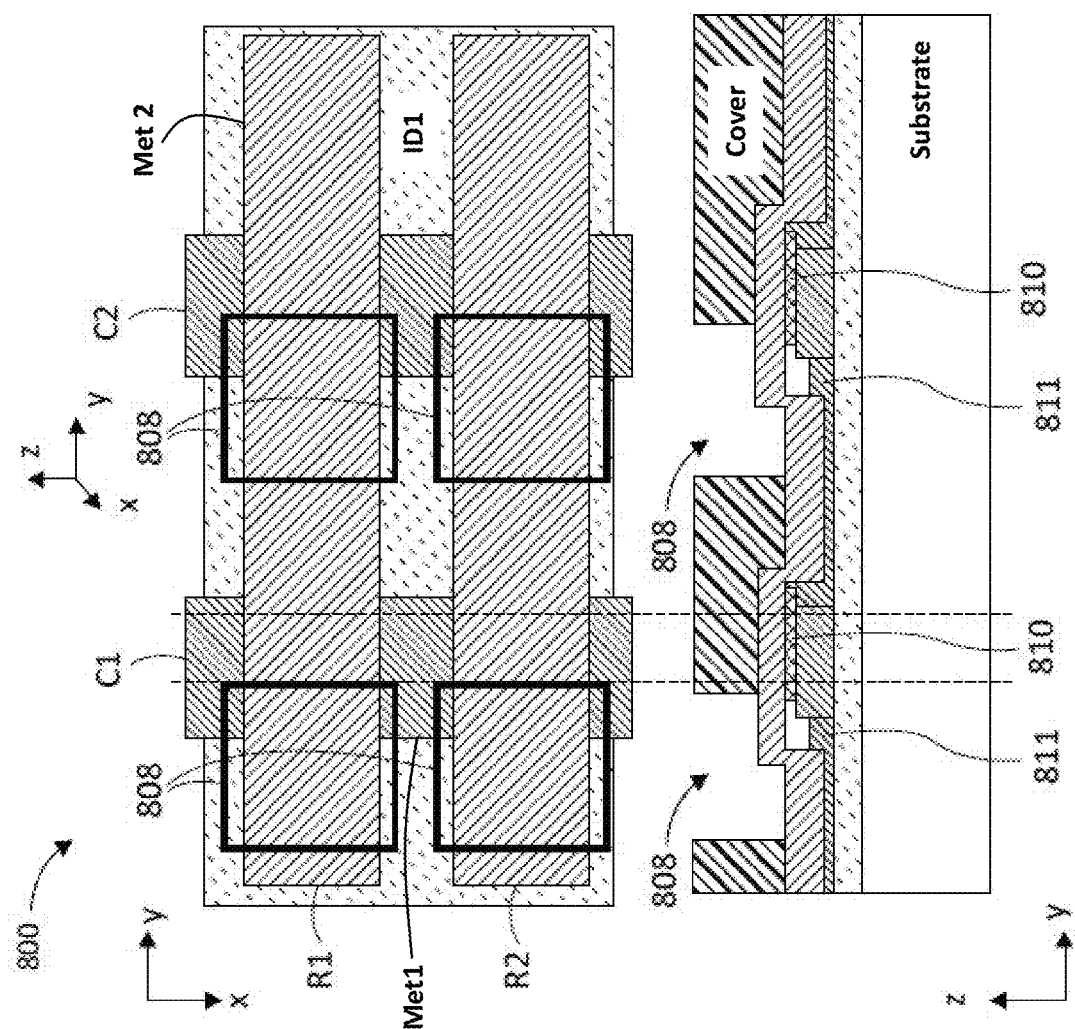
FIG. 8 illustrates an example bridge nanogap sensor assembly, according to some embodiments of the disclosure.

FIG. 8 illustrates another example of a horizontal nanogap sensor, namely, an example bridge nanogap sensor assembly 800 (top view in the plane x-y in the upper illustration and cross-sectional side view in the plane y-z in the lower illustration), according to some embodiments of the disclosure. Such a bridge structure may improve on the fully-released and partially-released cantilever structures as described above in that it reduces area overhead when packing a dense two-dimensional (2D) array of such nanogap sensors.

In various embodiments, the bridges (shown in FIG. 8) as bridges 802, can be fully-released or partially-released.

Various horizontal nanogap sensors described herein may be advantageously included in a sensor assembly where different sensors are arranged in rows and columns. A more practical illustration of an example assembly that includes horizontal nanogap sensors arranged in rows and columns is shown in FIG. 8, which will now be described.

FIG. 8 illustrates a top view (i.e., x-y plane) and a cross-sectional side view (i.e., z-y plane) of an example arrangement where horizontal nanogap sensors are arranged by having their top electrodes arranged in rows, namely in two rows labeled in FIG. 8 as R1 and R2, and their bottom electrodes arranged in columns, namely in two columns labeled in FIG. 8 as C1 and C2 (of course, in other embodiments, the bottom electrodes could be arranged in rows and the top electrodes—in columns, all of which embodiments being within the scope of the disclosure). The columns (i.e., the bottom electrodes) can be made from the electrically conductive material 202 described above, labeled as "Met1" in FIG. 8, while the rows (i.e., the top electrodes) can be made from the electrically conductive material 204 described above, labeled as "Met2" in FIG. 8, which, in various embodiments, could be the same or different materials. The "Substrate" shown in FIG. 8 could be the substrate 422 described above, and the "ID1" shown in FIG. 8 could be the insulator later 424 described above. Material shown as "Cover" in FIG. 8 could be any suitable cover material for containing the analytes within the nanogaps of the sensors. Fluidic windows for providing the analyte into the nanogaps can be seen in the cross-sectional side view of FIG. 8 as openings 808. A square outline in the top view of FIG. 8 illustrates an example boundary for such fluidic openings 808. In another embodiment of this sensor the entire overlap between e.g., R1 and C1 could be undercut by the nanogap etch process leaving no solid material connection between them. FIG. 8 further illustrates a top spacer material 810 provided on top of Met1 elements and a sidewall spacer material 811 provided on the sidewalls of Met1 elements. The top spacer material 810 may be the sacrificial material 210 described herein, removal (including at least partial removal) of which results in creation of a horizontal nanogap of a sensor, as shown in the bottom view of FIG. 8. The sidewall spacer material 811 may include any suitable insulator for providing separation (spacing) between the rows and the columns of the array 800. In this manner, the top electrodes (i.e., the rows in the example shown in FIG. 8), bridge over the bottom electrodes. Hence, the term "bridge nanogap sensor."

The bridge nanogap sensor assembly as e.g., shown in FIG. 8 may be fabricated as follows. Starting with a substrate 422, possibly with a layer of insulator 424 provided thereon, an electrically conductive material of the bottom electrode, e.g., the material 202 (e.g., Pt or Au), is deposited and patterned to form columns of the bottom electrodes, using any of the suitable processes described above. Then, the sidewall spacer material 811 is deposited and the overburden (i.e., excess) of the sidewall spacer material 811 is removed so that the sidewall spacer material 811 remains on the sidewalls of the columns of the bottom electrodes, but not on their upper surfaces. Next, the sacrificial material 810, e.g., SiN, is provided over the upper surfaces of the bottom electrodes. After that, an electrically conductive material of the top electrode, e.g., the material 202 (e.g., Pt or Au), is deposited and patterned to form rows of the top electrodes, using any of the suitable processes described above. At least portions of the sacrificial material 810 may then be removed, e.g., using a suitable etching technique, e.g., a suitable wet etch, to form horizontal nanogaps between overlapping portions of the bottom and top electrodes. A cover material, e.g., SU8 (a specific type of polymer often used in semiconductor manufacturing), or any other suitable material, may then be provided over the structure and the fluidic windows 808 may be formed therein.

A similar process flow may be used to fabricate an array of nanogap sensors as shown in FIG. 8 and described below.

Figure 9:
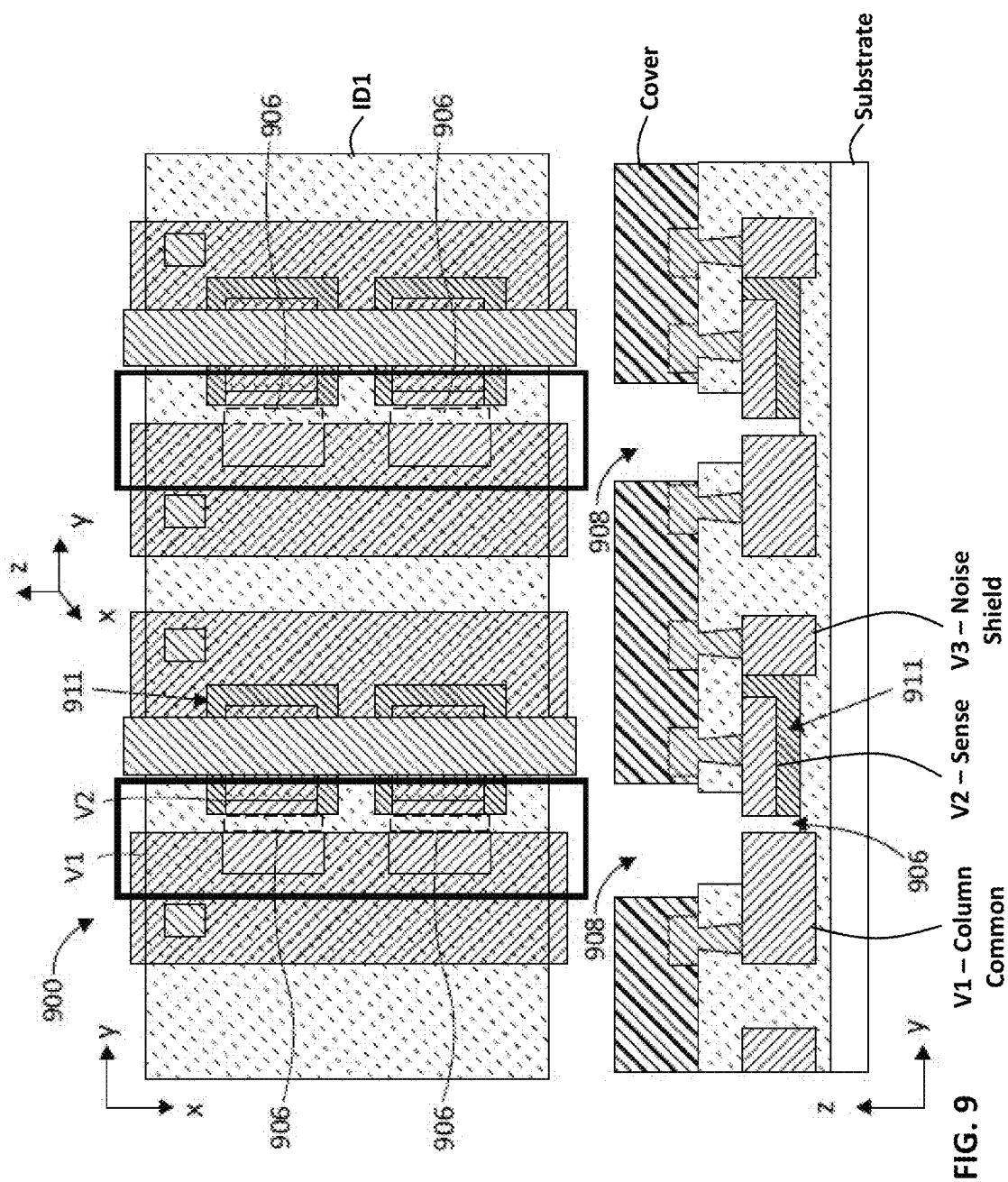
FIG. 9 illustrates an example vertical nanogap sensor array with noise shields using a single metal layer to form multiple electrodes, according to some embodiments of the disclosure.
Figure 10:
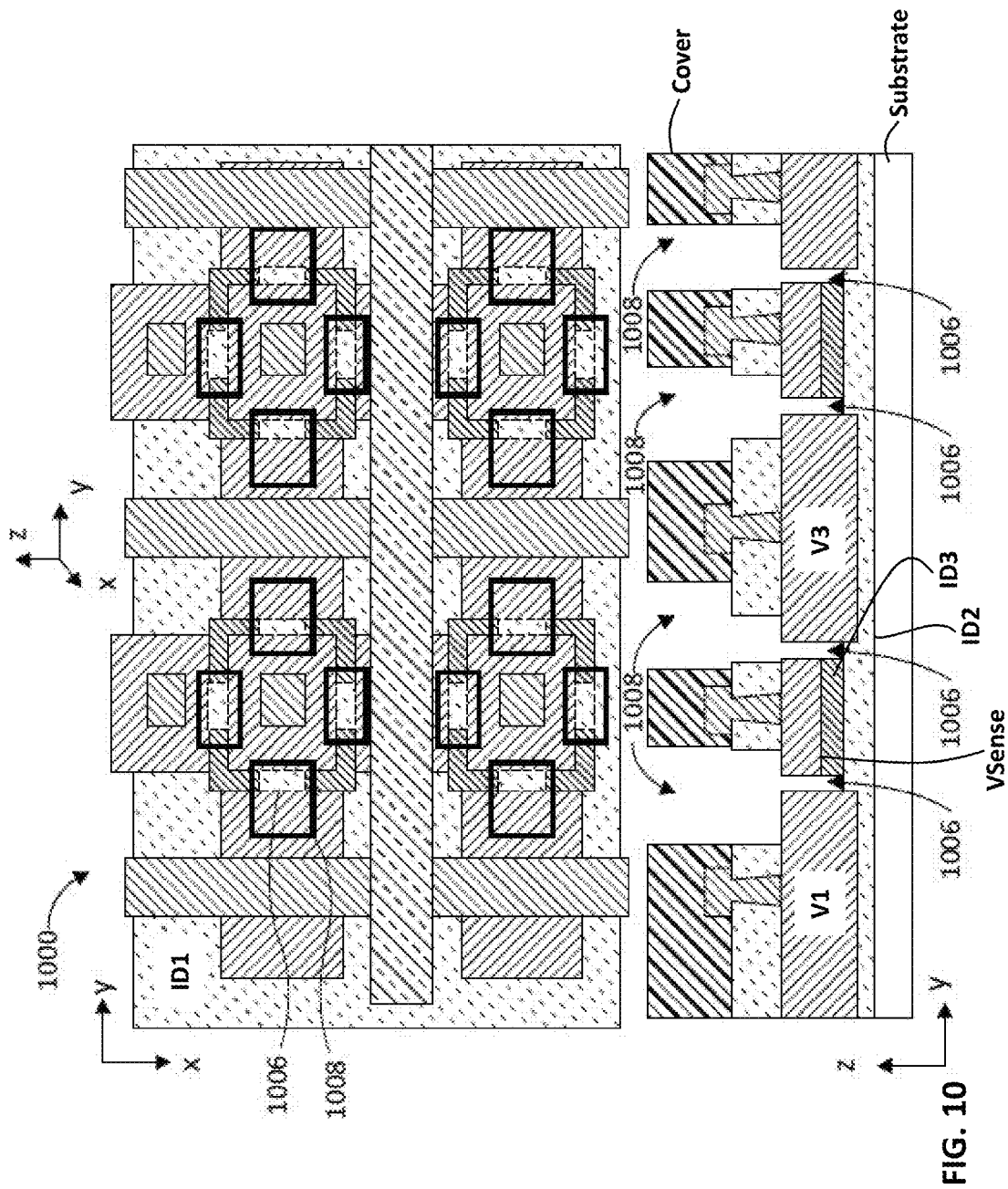
FIG. 10 illustrates an example vertical nanogap sensor array with high packing density using a single metal layer to form multiple electrodes, according to some embodiments of the disclosure.
Figure 11:
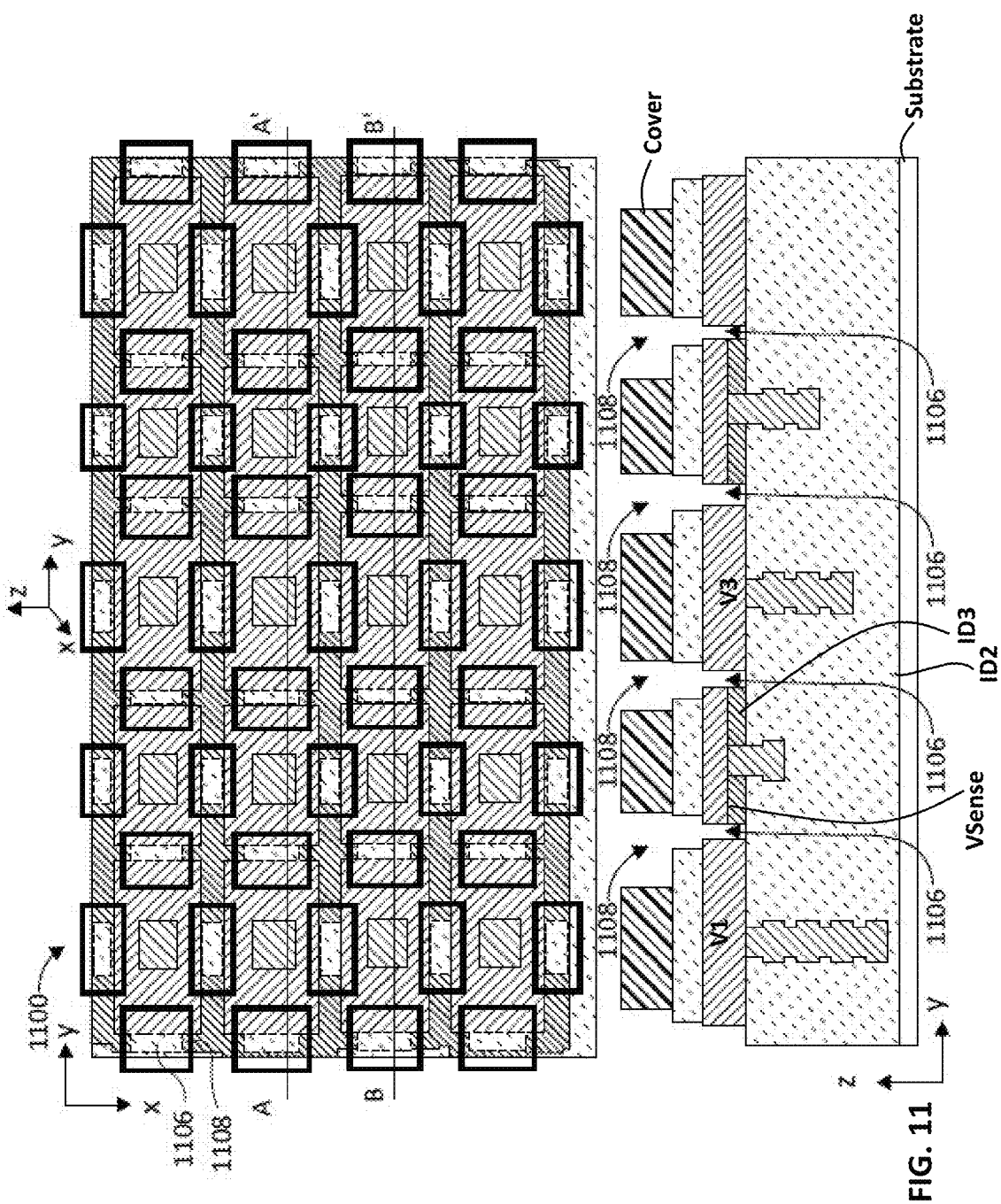
FIG. 11 illustrates an example vertical nanogap sensor array with high packing density using a single metal layer to form multiple electrodes with increased redundancy for each cell read, according to some embodiments of the disclosure.

FIGS. 9-11 illustrate various example vertical nanogap sensor arrays according to different embodiments of the disclosure. Similar to FIG. 8, each of FIGS. 9-11 provides a top view in the plane x-y in the upper illustration of the FIGS. and a cross-sectional side view in the plane y-z in the lower illustration.

FIG. 9 illustrates an example vertical nanogap sensor array 900 with noise shields using a single metal layer to form multiple electrodes, according to some embodiments of the disclosure.

While FIG. 8 illustrated an arrangement where horizontal nanogap sensors were arranged in rows and columns, FIG. 9 illustrates an example arrangement where vertical nanogap sensors are arranged in rows and columns. The "Substrate" shown in FIG. 9 could be the substrate 422 described above, and the "ID1" shown in FIG. 9 could be the insulator later 424 described above. Material shown as "Cover" in FIG. 9 could be any suitable cover material for containing the analytes within the nanogaps of the sensors. Fluidic windows for providing the analyte into the nanogaps are can be seen in the cross-sectional side view of FIG. 9 as openings 908. A rectangular outline in the top view of FIG. 9 illustrates an example boundary for such fluidic openings 908, illustrating that a single fluidic opening 908 may be shared among multiple vertical nanogap sensors. In other embodiments, each vertical nanogap sensor may have its own fluidic opening. FIG. 9 further illustrates a spacer material 911 for providing separation e.g., between V2 and V3 shown in FIG. 9. The spacer material 911 may e.g., be the sacrificial material 210 described above, where a portion of that material is removed to form the vertical nanogaps 906 in any of the manners described below, e.g., as described with reference to FIG. 12.

Further considerations for the vertical nanogap sensor assembly as e.g., shown in FIG. 9 are provided below.

In the sensor array 900, electrodes, made e.g., from Au or Pt, may be formed simultaneously, i.e., a single deposition can forms multiple, e.g., 3, electrodes shown in FIG. 9 as electrodes V1, V2, and V3. The electrode V1 may be a common column electrode, i.e., an electrode that is shared among multiple vertical nanogap sensors arranged in a column, as shown in the top view of FIG. 9 with V1 extending as a vertical line of material. The electrode V2 may be the other electrode of each vertical nanogap sensor, i.e., a different V2 would be provided for each sensor. The electrode V3 may, optionally, be used to serve as a noise shield.

The electrically conductive material(s) of the electrodes may be patterned, e.g., using lift-off or standard photolithography, to split into V1 and V3. Conformal SiN or similar sacrificial material which will result in formation of the nanogaps 906 when the material is removed may be used. Only one edge of SiN formed gap may be used for sensing to ensure maximum reproducibility. Fluidic windows (or access ports) 908 (similar to 208 shown in FIG. 2A) provided in a cover layer, e.g., polymer cover layer, could be patterned to form individual openings/wells per sensor. In the sensor array 900 shown in FIG. 9, fluidic ports are arranged so that columns are individually addressable. In other embodiments, other arrangements of the fluidic windows are possible and are within the scope of the disclosure.

Au or Pt electrode (V1) may be used as column common, sensing electrode (V2) may be wired out in row or column format (there is a need to change nanogap location to suit if row access format is used), Side electrode (V3) may be used as a shield against electromagnetic interference and wired to noise ground.

In some embodiments, electrodes V1 and V3 could be formed with one metal type (e.g., Pt) and V2 could be formed with a second metal type e.g., Au as in FIG. 10. Due to different work functions there may be some advantage in tunneling.

FIG. 10 illustrates an example vertical nanogap sensor array 1000 with high packing density using a single metal layer to form multiple electrodes, according to some embodiments of the disclosure.

Similar to FIG. 9, FIG. 10 illustrates an example arrangement where vertical nanogap sensors are arranged in rows and columns. FIG. 10 and FIG. 11 show one embodiment where four sensors share a common central electrode. Examples of other embodiments include a hexagonal lattice packing where six sensors would share a common central electrode or a triangular lattice where three sensors share a common central electrode.

The "Substrate" shown in FIG. 10 could be the substrate 422 described above, and the "ID2" shown in FIG. 10 could be the insulator later 424 described above. "ID1" shown in FIG. 10 could be any other interlayer dielectric material commonly used in semiconductor manufacturing. Material shown as "Cover" in FIG. 9 could be any suitable cover material for containing the analytes within the nanogaps of the sensors. Fluidic windows for providing the analyte into the nanogaps are can be seen in the cross-sectional side view of FIG. 10 as openings 1008. Rectangular outlines in the top view of FIG. 10 illustrate example boundaries for such fluidic openings 1008, illustrating an individual fluidic window 1008 for each of the multiple vertical nanogap sensors. In other embodiments, at least some of the vertical nanogap sensor may share a single fluidic opening. FIG. 10 further illustrates a spacer material "ID3" for providing separation e.g., between Vsense and V1, V3 shown in FIG. 10. The spacer material ID3 may e.g., be the sacrificial material 210 described above, where a portion of that material is removed to form the vertical nanogaps 1006 in any of the manners described below, e.g., as described with reference to FIG. 12.

Further considerations for the vertical nanogap sensor assembly as e.g., shown in FIG. 10 are provided below.

In the sensor array 1000, electrodes, made e.g., from Au or Pt, may be formed simultaneously, i.e., a single deposition can forms multiple electrodes V1, Vsense, and V3. Electrodes may be patterned, e.g., using lift-off or standard photolithography, to split into multiple electrodes around "center" sense electrode Vsense. Conformal SiN or similar sacrificial material which will result in formation of the nanogaps 1006 when the material is removed may be used as interlayer dielectric shown in FIG. 10 as ID3. Nanogaps 1006 at each edge of the sense electrode Vsense may be used for improved packing density.

Fluidic windows (or access ports) 1008 (similar to 208 shown in FIG. 2A) provided in a cover layer, e.g., polymer cover layer, could be used for flood fill of the entire sensor array structure, which advantageously would be hydrophobic in nature. In some embodiments, the base of the fluidic windows 1008 could be hydrophilic to ensure fluid stays therein; thus when the flood fill is cleared, wells should stay full but fluidically isolated as the hydrophobic cover top surface will repel fluid but the hydrophilic well 1008 bottom surface would act to retain its fluid.

At least 3 layer metal interconnect may be used under or over Au/Pt electrodes (only 2 levels shown in the top view of FIG. 10, in order to not clutter the drawing).

In some embodiments, electrodes V1 and V3 could be formed with one metal type (e.g., Pt) and V2 could be formed with a second metal type. Due to different work functions there may be some advantage in tunneling.

FIG. 11 illustrates an example vertical nanogap sensor array 1100 with high packing density using a single metal layer to form multiple electrodes with increased redundancy for each cell read, according to some embodiments of the disclosure.

Similar to FIGS. 9 and 10, FIG. 11 illustrates an example arrangement where vertical nanogap sensors are arranged in rows and columns. The "Substrate" shown in FIG. 11 could be the substrate 422 described above, and the "ID2" shown in FIG. 11 could be the insulator later 424 described above. "ID1" shown in FIG. 11 could be any other interlayer dielectric material commonly used in semiconductor manufacturing. Material shown as "Cover" in FIG. 11 could be any suitable cover material for containing the analytes within the nanogaps of the sensors. Fluidic windows for providing the analyte into the nanogaps are can be seen in the cross-sectional side view of FIG. 11 as openings 1108. Rectangular outlines in the top view of FIG. 11 illustrate example boundaries for such fluidic openings 1108, illustrating an individual fluidic window 1108 for each of the multiple vertical nanogap sensors. In other embodiments, at least some of the vertical nanogap sensors may share a single fluidic opening. FIG. 11 further illustrates a spacer material "ID3" for providing separation e.g., between Vsense and V1, V3 shown in FIG. 11. The spacer material ID3 may e.g., be the sacrificial material 210 described above, where a portion of that material is removed to form the horizontal nanogaps 1106 in any of the manners described below, e.g., as described with reference to FIG. 12.

Further considerations for the vertical nanogap sensor assembly as e.g., shown in FIG. 11 are provided below.

Similar to the array 1000, in the sensor array 1100, electrodes, made e.g., from Au or Pt, may be formed simultaneously, i.e., a single deposition can forms multiple electrodes V1, Vsense, and V3. Electrodes may be patterned, e.g., using lift-off or any standard photolithography process, to split into multiple electrodes around "center" sense electrode Vsense. Conformal SiN or similar sacrificial material which will result in formation of the nanogaps 1106 when the material is removed may be used as interlayer dielectric shown in FIG. 11 as ID3. Nanogaps 1106 at each edge of sense electrode Vsense may be used for improved packing density and redundancy advantage (i.e., if one nanogap blocked or inactive then 3 others are still available). Given the nanometer scale of the nanogaps it is occasionally possible that a nanogap would be or become blocked or obstructed during or manufacture. The scheme shown in FIG. 10 and FIG. 11 allows in certain embodiments for any of the four nanogaps to be used for sensing. Electrical means can be used to determine which of the gaps is functional before the analyte is used or indeed during a read sequence. In other embodiments of the invention, if more than one nanogap is functional, each of the four nanogaps contacted by Exy in FIG. 11 around Sij will provide a signal which can then be compared in the subsequent signal processing block to improve the reliability of the detection.

Sensor reading scheme—many variations possible but simplest is (t=0) all nodes at 0; (t=1) raise e.g., S11 and read quadruplicate signal from E11, E12, E01 and E21; (t=2) all nodes zero; (t=3 etc.) repeat dropping down a row. This requires separate Exy and Sij row and column lines.

Considerations provided for the fluidic windows 1008 are applicable to the fluidic windows 1108 and, therefore, are not repeated here.

In some embodiments, electrodes V1 and V3 could be formed with one metal type (e.g., Pt) and V2 could be formed with a second metal type. Due to different work functions there may be some advantage in tunneling.

In this version a multiple level metal interconnect scheme (at least 4 levels, more would be advantageous) such as widely used as standard on VLSI digital IC chips may be used. Due to array complexity, it may be preferable to use interconnect organized in a "bottom up" configuration (i.e., no wiring above sensors), as can be seen in the cross-sectional side view of FIG. 11. Note that a cross-section along the plane B-B' shown in the top view of FIG. 11 would be the same as a cross-section across the plane A-A' except shifted left or right by one cell and metal interconnection levels change.

Figure 12:
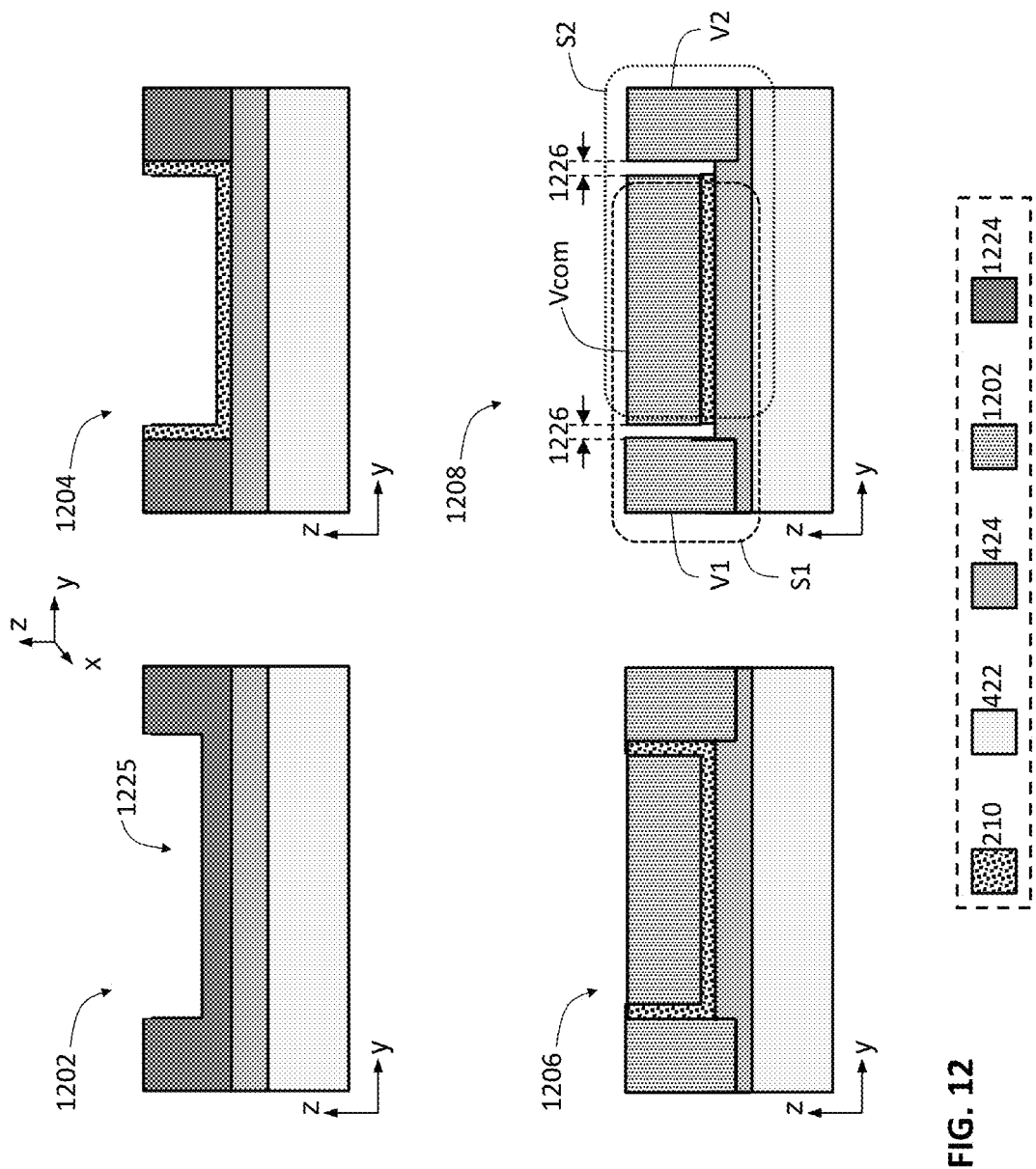
FIG. 12 illustrates example steps for fabricating a first vertical nanogap sensor, according to some embodiments of the disclosure.

FIGS. 12-14 now describe example methods for fabricating a vertical nanogap sensors according to various embodiments of the disclosure. Any of these vertical nanogap sensors may be used in sensor arrays such as e.g., in any one of the arrays shown in FIGS. 9-11. Each of FIGS. 9 and 14 provides only a cross-sectional side view in the plane y-z of the coordinate system used in the FIGS., while FIG. 13 provides a cross-sectional side view in the plane y-z in the upper illustration of the FIG. and a top view in the plane x-y in the lower illustration.

FIG. 12 illustrates example steps for fabricating a first vertical nanogap sensor, according to some embodiments of the disclosure. On a high-level, the steps of FIG. 12 may be summarized as creating a U-shaped liner of a sacrificial material (e.g., SiN) inside an insulator (e.g., an oxide such as e.g., SiO) mold, then removing the mold material, and replaces the mold material with a noble metal (e.g., Au or Pt) which will serve as electrodes of a nanogap sensor, with some of the sacrificial material removed to form one or more nanogaps.

The method of FIG. 12 may begin starting with a substrate 422 as described above, which may, optionally, include a layer of an insulating material over it, e.g., a layer of a silicon oxide 424 as described above, over which an additional layer of insulator, e.g., another silicon oxide layer 1224, is provided, in which an opening 1225 is formed, as shown with a structure 1202 illustrated in FIG. 12. In some embodiments, the first dielectric layer 424 could be a high density low etch rate layer and the additional dielectric layer 1224 could be a low density high etch rate layer in order to provide a measure of self-limiting for the subsequent revealing etch which will clear the sacrificial 210 layer top edges. In other embodiments, layers 424 and 1224 may be provided as a single layer in which an opening 1225 is formed. As will become clear from the description below and the illustrations, sidewalls of the opening 1225 will later become part of vertical nanogaps of the sensor. In various embodiments, a depth of the opening 1225 (i.e., a dimension measured along the z axis of the coordinate system shown in the FIGS.) may be between about 200 and 2000 nm, including all values and ranges therein, e.g., between about 100 and 1500 nm, or between about 150 and 500 nm, a length of the opening 1225 (i.e., a dimension measured along the y-axis of the coordinate system shown in the FIGS.) may be between about 100 and 10000 nm, including all values and ranges therein, e.g., between about 200 and 5000 nm, or between about 500 and 1000 nm, and a width of the opening 1225 (i.e., a dimension measured along the x-axis of the coordinate system shown in the FIGS.) may be between about 100 and 20000 nm, including all values and ranges therein, e.g., between about 500 and 10000 nm, or between about 1000 and 5000 nm.

Next, a layer of the sacrificial material 210 is deposited, as described above, e.g., deposited using any of the known conformal deposition techniques, on the inner sidewalls and openings of the opening 1225, thus lining the opening 1225 with a thin layer of the sacrificial material, as shown with a structure 1204 illustrated in FIG. 12. In some embodiments, the thickness of the sacrificial material layer 210 may be on the order of the desired nanogap thickness, e.g., between about 1 and 200 nm, including all values and ranges therein (e.g., about 20 nm), e.g., between about 5 and 100 nm, or between about 5 and 50 nm. In some embodiments, the sacrificial material 210 used in the structure 1204 may be SiN.

Next, an electrically conductive material 1202 is deposited over the structure 1204, and then planarized to expose the sacrificial material 210, as shown in FIG. 12 with a structure 1204. The electrically conductive material 1202 may be any of the electrically conductive materials described above, e.g., any of the materials used as the materials 202 or 204 described above, and may be deposited using deposition techniques described above. In some embodiments, the electrically conductive material 1202 may include Au or Pt, and the sacrificial material 210 may include SiN. The planarization may include chemical mechanical planarization (CMP), using a suitable slurry formulation and mechanical polishing process to remove unwanted materials from the structure, achieving a relatively smooth upper surface upon which further components may be built.

The method may further include a step of etching the sacrificial material 210, e.g., using wet etch, to remove the material 210 from the side walls of the opening 1225, forming a nanogap 1226, thus resulting in a vertical nanogap sensor as shown with a structure 1208 in FIG. 12. The structure 1208 may be seen as showing two vertical nanogap sensors, labeled in FIG. 12 as a first sensor S1 (indicated with a dashed contour in FIG. 12) and a second sensor S2 (indicated with a dotted contour in FIG. 12), sharing a common electrode Vcom in between. The first sensor S1 then has a second electrode across from the nanogap 1226 shown on the left side of the structure 1208, the second electrode of the first sensor labeled in FIG. 12 as an electrode V1, while the second sensor S2 has a second electrode across from the nanogap 1226 shown on the right side of the structure 1208, the second electrode of the second sensor labeled in FIG. 12 as an electrode V2.

Figure 13A:
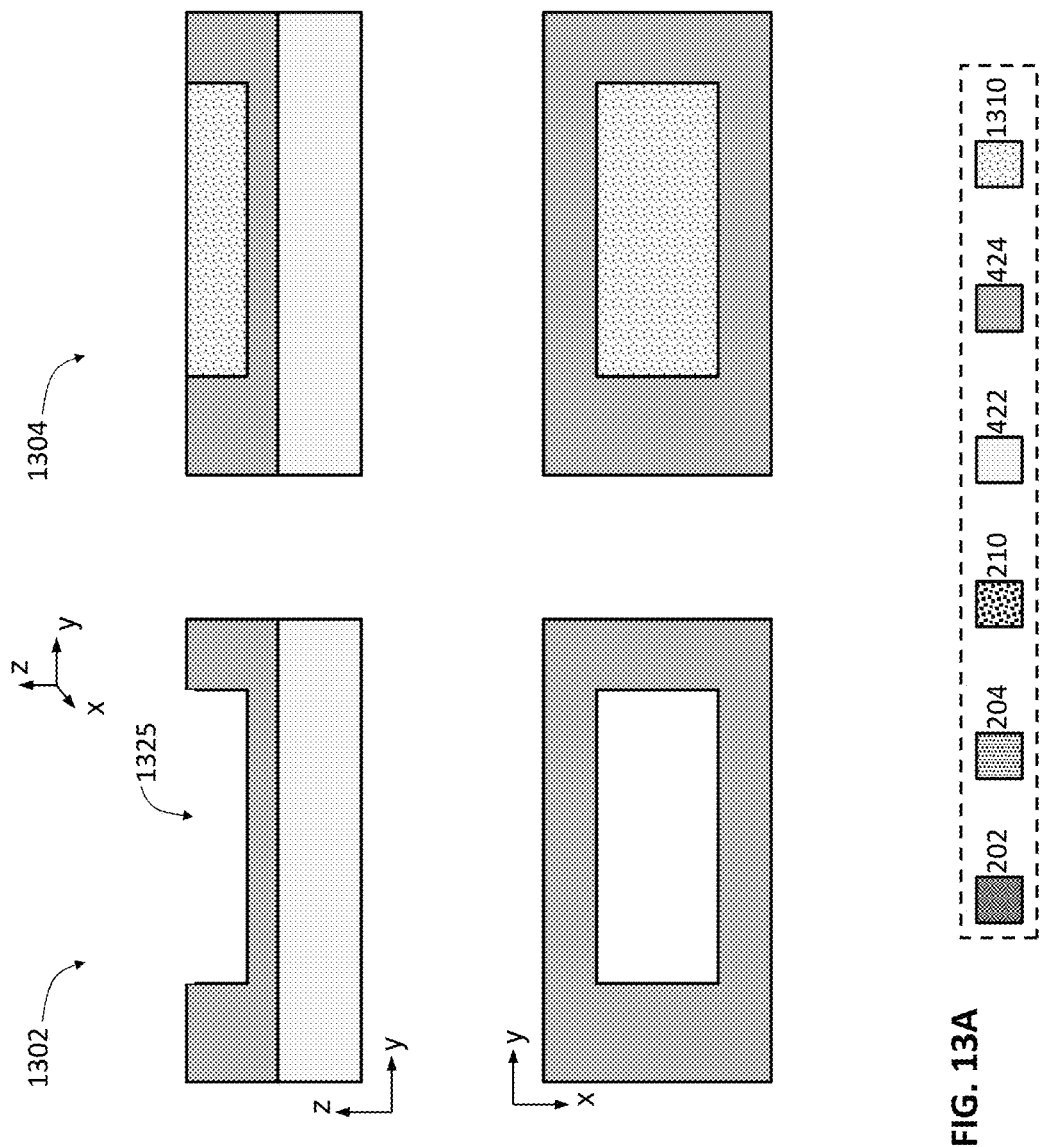
FIGS. 13A-13C illustrate example steps for fabricating a second vertical nanogap sensor, according to some embodiments of the disclosure.
Figure 13B:
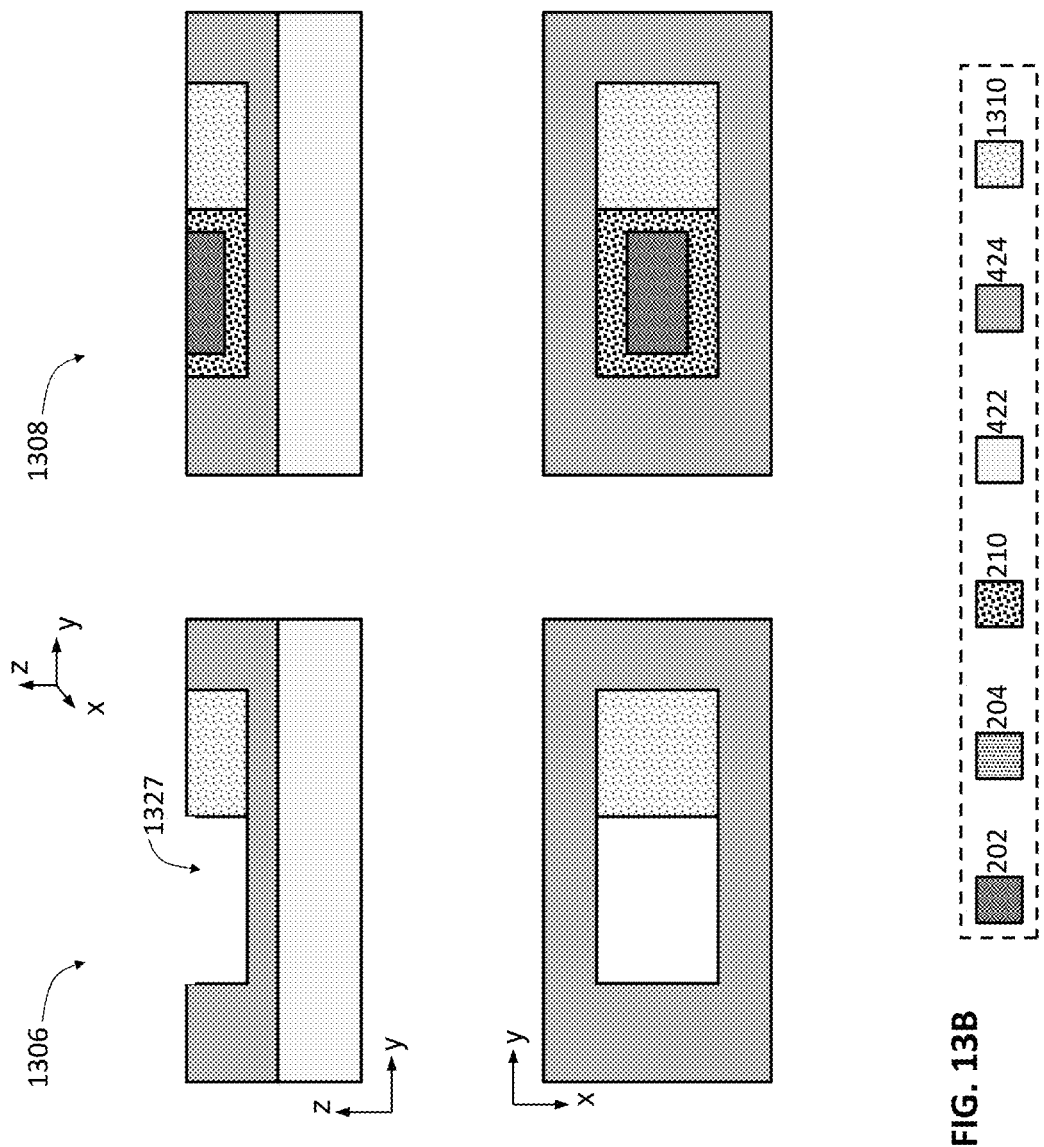
Figure 13C:
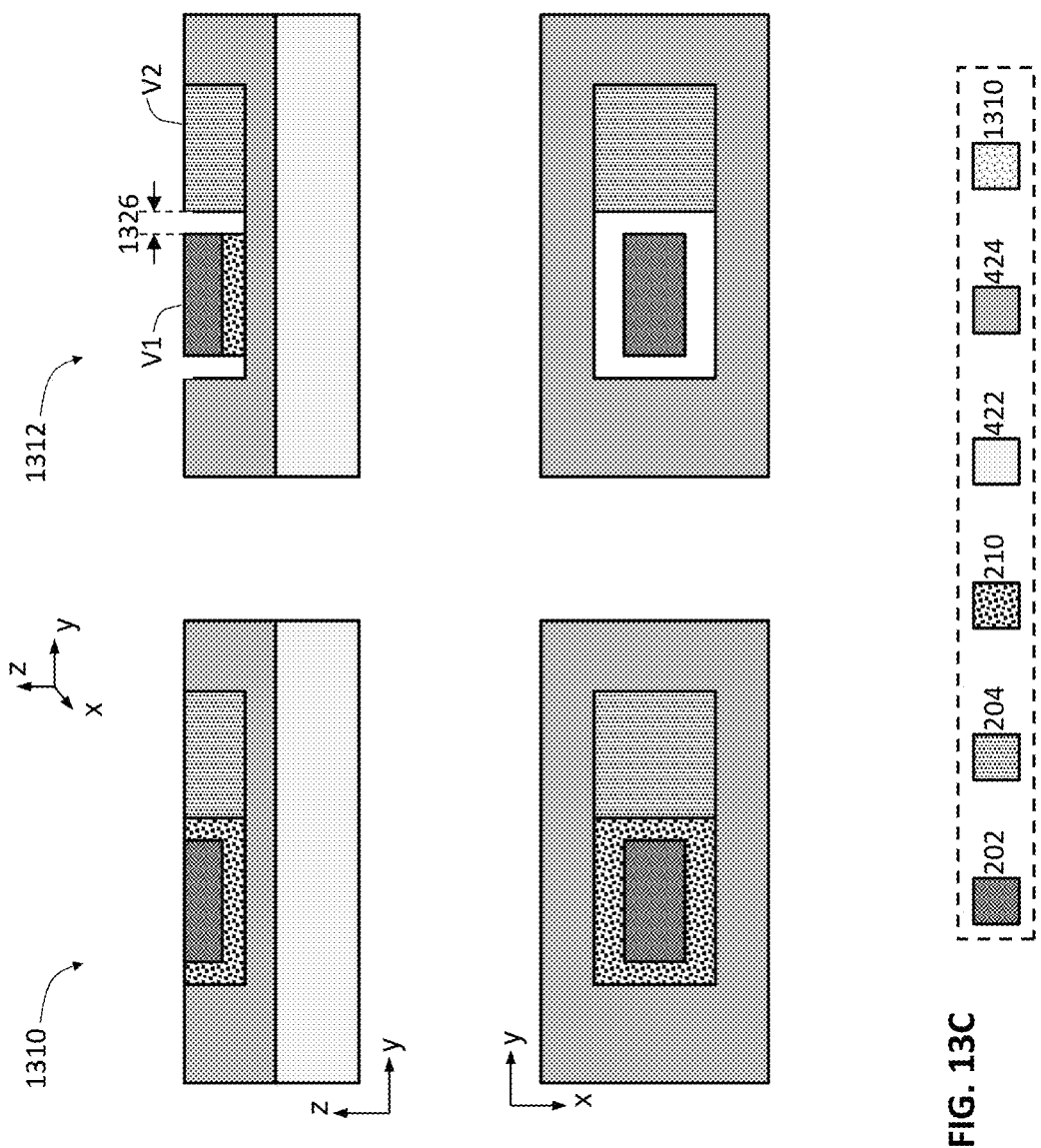

FIGS. 13A-13C illustrate example steps for fabricating a second vertical nanogap sensor, according to some embodiments of the disclosure. On a high-level, the steps of FIGS. 13A-13C may be summarized as etching a pit and using a sacrificial material (e.g., a sacrificial metal such as e.g., TiW) which is later replaced by a noble metal (e.g., Pt), particularly suitable for sharing a single electrode among multiple vertical nanogap sensors.

The method of 13A-13C may begin starting with a substrate 422 as described above, which may, optionally, include a layer of an insulating material over it, e.g., a layer of a silicon oxide 424 as described above, in which an opening 1325 is formed, as shown with a structure 1302 illustrated in FIG. 13A. As will become clear from the description below and the illustrations, one or more sidewalls of the opening 1325 will later become part of vertical nanogaps of the sensor. The opening 1325 may have dimensions along z axis and x-axis substantially as those described above for the opening 1225, but be somewhat larger in the dimension of the y-axis, e.g., 1.5 to 3 times larger than the opening 1225, because later on the opening 1325, when filled with a sacrificial material 1310, will include a sub-opening 1327 within which sub-opening will have dimensions comparable to that of the opening 1225.

Next, a layer of the sacrificial material 1310 is deposited into the opening 1325 and, possibly, followed up by a planarization, to result in a structure 1304 as shown in FIG. 13A. Considerations provided above for the sacrificial material 210 are applicable to the sacrificial material 1310 and, therefore, not repeated here. In some embodiments, the sacrificial material 1310 may be a sacrificial metal, such as e.g., TiW.

After that, a portion of the sacrificial material 1310 is removed on one side of the opening 1325, forming a smaller opening 1327, as shown with a structure 1306 in FIG. 13B. The opening 1327 may have dimensions substantially as those described above for the opening 1225 as described above.

A conformal layer of the sacrificial material 210 is then provided, e.g., deposited using any of the known conformal deposition techniques, on the inner sidewalls and openings of the opening 1327, thus lining the opening 1327 with a thin layer of the sacrificial material, and a first electrically conductive material, e.g., a material such as the material 202, is deposited into the lined opening 1327 (possibly planarized to expose the sacrificial materials 210 and 1310), as shown with a structure 1308 illustrated in FIG. 13B. In some embodiments, the thickness of the sacrificial material layer 210 in the structure 1308 may be comparable to that of in the structure 1204 shown in FIG. 12. Considerations provided with respect to deposition techniques and materials used provided for similar process steps above are applicable here and not repeated. In some embodiments, the electrically conductive material 202 may include Au or Pt, and the sacrificial material 210 may include SiN. The planarization may include CMP.

The remaining portion of the sacrificial material 1310 may then be removed, and a resulting opening filled with a second electrically conductive material, e.g., the material 204 as described above, as shown with a structure 1310 in FIG. 13C. Considerations provided with respect to deposition techniques and materials used provided for similar process steps above are applicable here and not repeated.

The method may further include a step of etching the sacrificial material 210, e.g., using wet etch, to remove the material 210 from the side walls of the opening 1327, forming a nanogap 1326, thus resulting in a vertical nanogap sensor as shown with a structure 1312 in FIG. 13C. Considerations provided with respect to deposition techniques and materials used provided for similar process steps above are applicable here and not repeated. Elements formed of the first and second electrically conductive materials 202 and 204 form the electrodes V1 and V2, respectively, around the vertical nanogap 1326.

In some implementations, multiple vertical nanogap sensors, sharing one of the electrodes, e.g., electrode V1, may be formed in a single fabrication process, as shown with a structure 1500 shown in FIG. 15 and described in greater detail below.

Figure 14A:
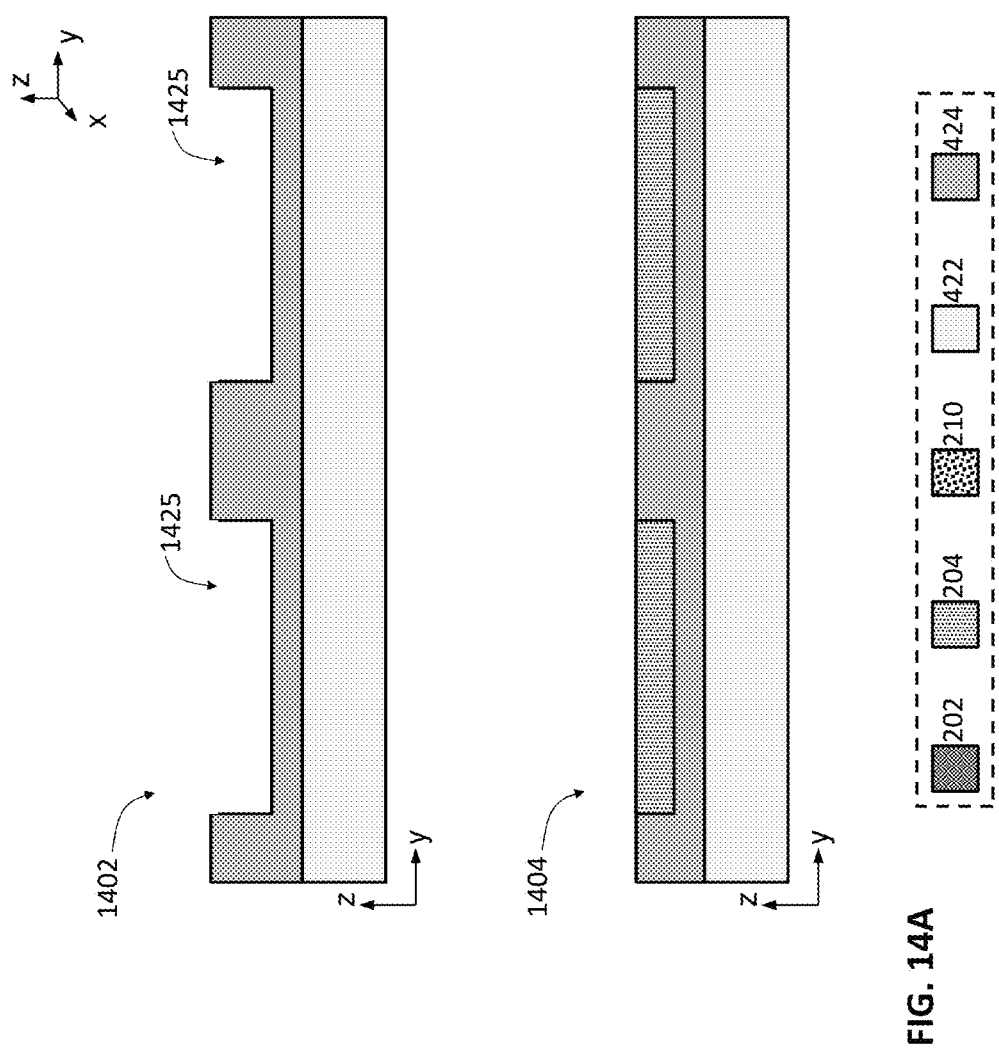
Figure 14B:
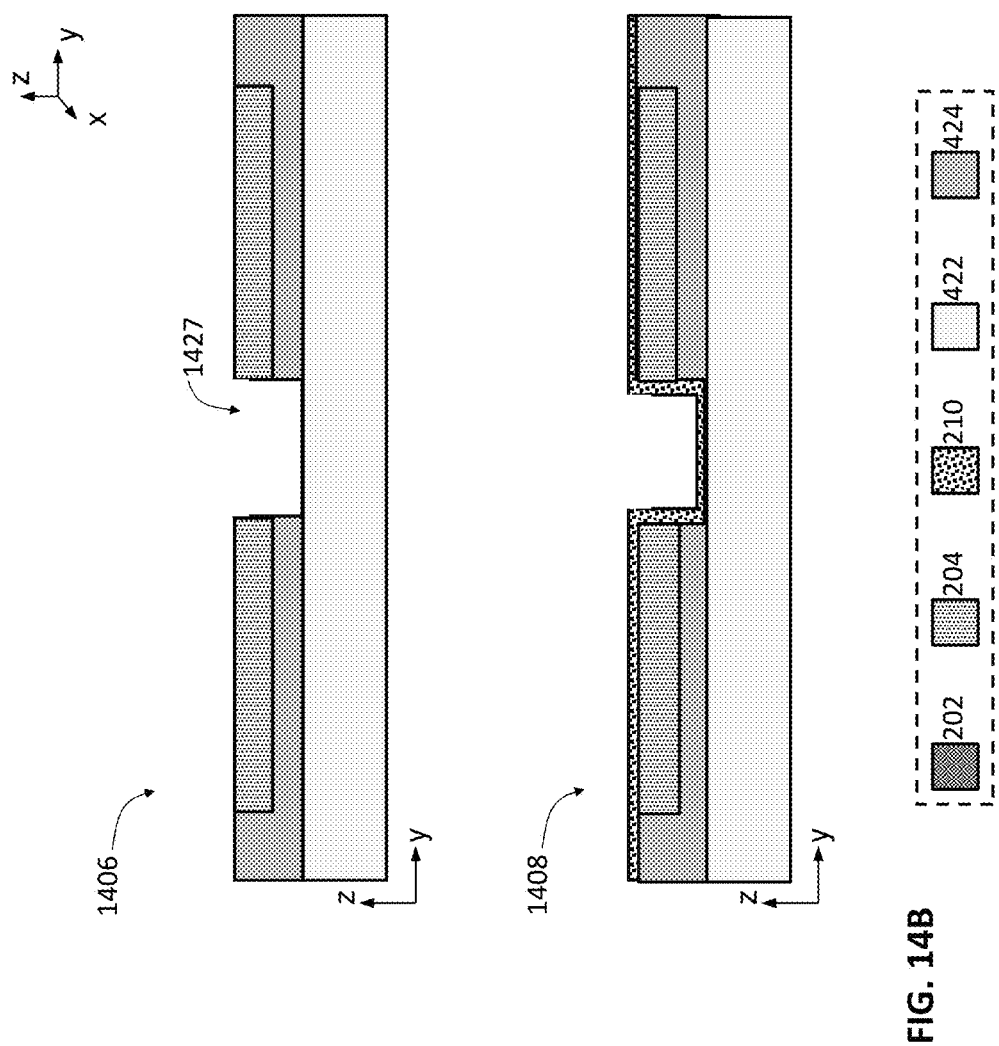

FIGS. 14A-14C illustrate example steps for fabricating a third vertical nanogap sensor, according to some embodiments of the disclosure.

The method of FIGS. 14A-14C may begin starting with a substrate 422 as described above, which may, optionally, include a layer of an insulating material over it, e.g., a layer of a silicon oxide 424 as described above, in which two openings 1425 are formed, as shown with a structure 1402 illustrated in FIG. 14A. As will become clear from the description below and the illustrations, sidewalls of the openings 1425 which are facing one another (i.e., a sidewall of one of the openings 1425 facing a sidewall of the other one of the openings 1425) will later become part of vertical nanogaps of the sensor. The distance between the openings 1425 (i.e., a dimension measured along the y-axis) may be comparable to the y-axis dimension of the opening 1225, described above.

Next, the openings 1425 are filled with an electrically conductive material, e.g., the material 204 as described above, and planarized, as shown with a structure 1404 in FIG. 14A. Considerations provided with respect to deposition techniques and materials used provided for similar process steps above are applicable here and not repeated. In some embodiments, the electrically conductive material 204 may include Pt.

Next, the material between the openings 1425 is removed, e.g., using wet etch, forming an opening 1427 in between, the original openings 1425, as shown with a structure 1406 in FIG. 14B.

A conformal layer of the sacrificial material 210 is then provided, e.g., deposited using any of the known conformal deposition techniques, on the inner sidewalls and openings of the opening 1427, thus lining the opening 1427 with a thin layer of the sacrificial material, as shown with a structure 1408 illustrated in FIG. 14B. In some embodiments, the thickness of the sacrificial material layer 210 in the structure 1408 may be comparable to that of in the structure 1204 shown in FIG. 12. Considerations provided with respect to deposition techniques and materials used provided for similar process steps above are applicable here and not repeated.

Next, the opening 1427 lined with the sacrificial material 210 is filled with an electrically conductive material, e.g., the material 202 as described above, as shown with a structure 1410 in FIG. 14C. Considerations provided with respect to deposition techniques and materials used provided for similar process steps above are applicable here and not repeated. In some embodiments, the electrically conductive material 202 may include Au and the sacrificial material 210 may include one or more of TiW, Al2O3, and AlN.

The method may conclude with a step of planarizing the electrically conductive material deposited as shown with the structure 1410, and etching the sacrificial material 210, e.g., using wet etch, to remove the material 210 from the side walls of the opening 1427, forming nanogaps 1426, thus resulting in a vertical nanogap sensor as shown with a structure 1412 in FIG. 14C. Considerations provided with respect to deposition techniques and materials used provided for similar process steps above are applicable here and not repeated.

The structure 1412 may be seen as showing two vertical nanogap sensors, labeled in FIG. 14C as a first sensor S1 (indicated with a dashed contour in FIG. 14C) and a second sensor S2 (indicated with a dotted contour in FIG. 14C), sharing a common electrode Vcom in between, which could be the "first electrode" of the sensors S1 and S2. The first sensor S1 then has a second electrode across from the nanogap 1426 shown on the left side of the structure 1412, the second electrode of the first sensor labeled in FIG. 14C as an electrode V1, while the second sensor S2 has a second electrode across from the nanogap 1426 shown on the right side of the structure 1412, the second electrode of the second sensor labeled in FIG. 14C as an electrode V2.

Figure 15:
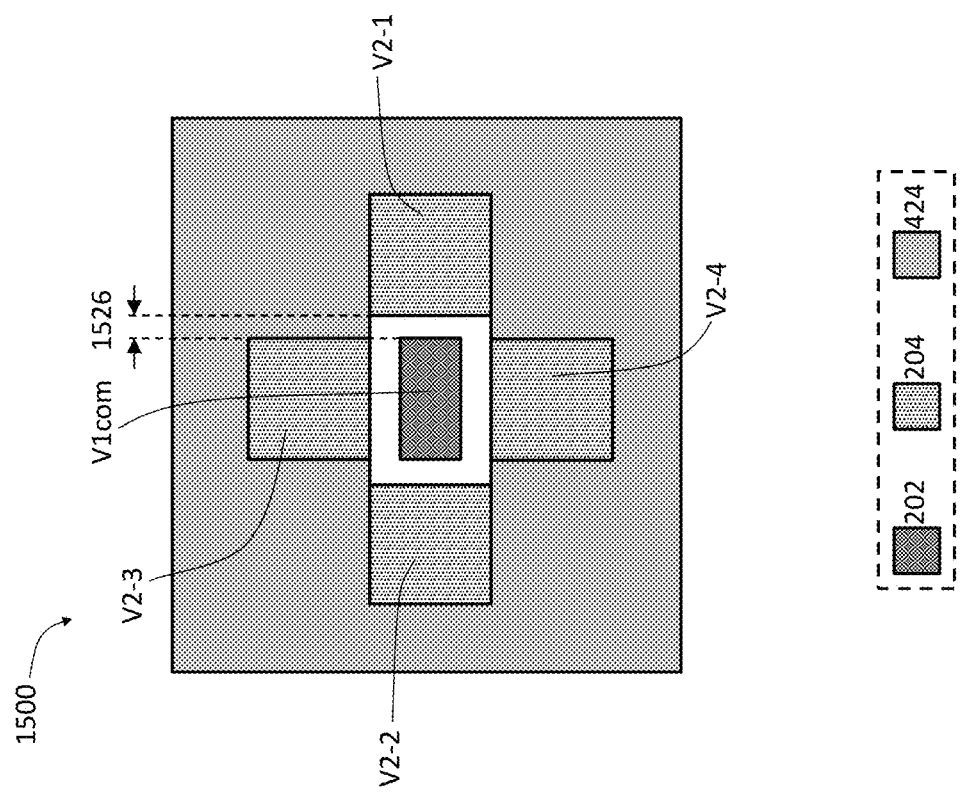
FIG. 15 illustrates an example vertical nanogap sensor arrangement where multiple vertical sensors share a common electrode, according to some embodiments of the disclosure.

FIG. 15 illustrates an example vertical nanogap sensor arrangement 1500 where multiple vertical sensors share a common electrode, according to some embodiments of the disclosure. In particular, FIG. 15 illustrates a common first electrode, labeled as V1com, shared between four vertical nanogap sensors, in each of which sensors a separate second electrode, labeled in FIG. 15 as electrodes V2-1, V2-2, V2-3, and V2-4 for the four sensors, is separated from the first shared electrode V1com by a respective nanogap 1526 (only one such nanogap is specifically labeled in FIG. 15 in order to not clutter the drawing). In various other embodiments, any number of vertical nanogap sensors other than the 4 shown in FIG. 15 may be used, e.g., 2 or 3 nanogap sensors. Furthermore, while FIG. 15 illustrates vertical nanogap sensors of the type shown in FIG. 13C, such electrode sharing may be similarly implemented for other vertical nanogap sensors proposed herein.

Electrode sharing may advantageously save space on a chip implementing multiple nanogap sensors as described herein, thus enabling tight packing of arrays of nanogap sensors, which would be particularly useful for DNA sensors.

Figure 16:
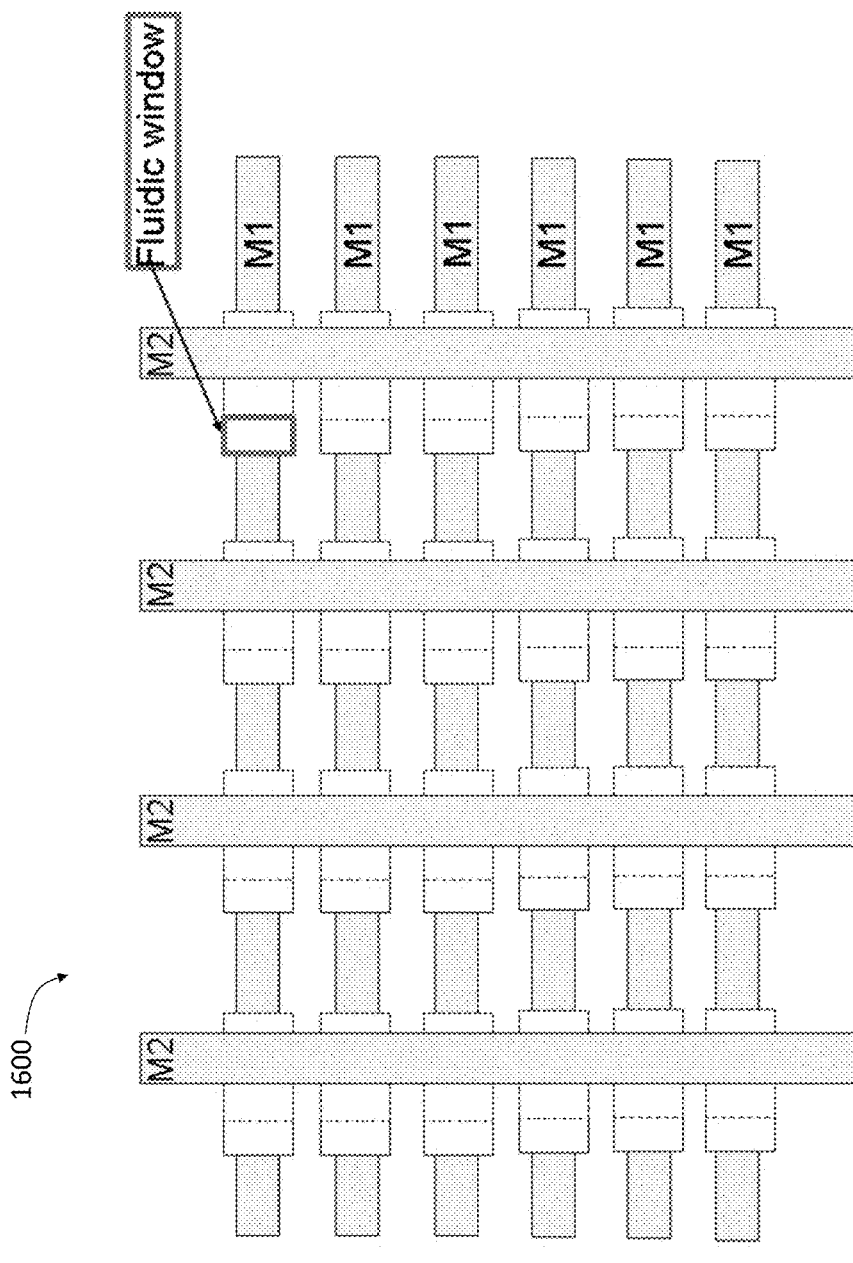
FIG. 16 illustrates an example vertical nanogap sensor arrangement where multiple horizontal sensors share a common electrode, according to some embodiments of the disclosure.

Some arrangements for electrode sharing for horizontal nanogap sensors was shown in FIGS. 5B and 5C and described above. FIG. 16 illustrates another example nanogap sensor arrangement 1600 where multiple sensors share a common electrode, according to some embodiments of the disclosure. A metal 1 trace runs along the rows underneath the sensors, while a metal 2 trace runs above the sensors along the columns. FIG. 16 shows one embodiment where each sensor has its own individual and separate fluidic window. In other embodiment, the fluidic window can be shared across multiple sensors to simplify the fabrication process flow or allow tighter packing of the devices. In this embodiment the electrode materials themselves do not form the interconnection wiring but more standard aluminum or copper could be used. Materials suitable for the electrodes may not always make the best interconnection wiring materials for cost or ease of manufacture reasons.

Notes on Fabrication Techniques

In various embodiments of fabricating nanogap sensors as proposed herein, nanoimprint lithography methods and offset printing techniques may be used.

In some embodiments, direct-write techniques may be used for fabricating at least some of the nanogap sensors described herein. In general, direct-write techniques include creating one sensor at a time by directly "writing" on a wafer with a particle beam (i.e., a "pen") of photons, ions, or electrons.

When direct-write techniques implement writing using photons (i.e., laser writing), the smallest definable feature may be limited to the side of a diffraction-limited laser spot, which may be on the order of the wavelength of the laser light used, divided by the numerical aperture (NA). The smallest holes would thus likely have to be larger than about 10 nm. When direct-write techniques implement writing using ions (i.e., ion beam lithography), a focused ion beam (FIB) can be used to drill holes into a membrane to create nanopores or into a substrate (for nanowells). When direct-write techniques implement writing using electrons (i.e., electron-beam lithography), an electron beam may be directed towards the semiconductor surface to ablate atoms away and create nanometric openings.

Example Data Processing System

Figure 17:
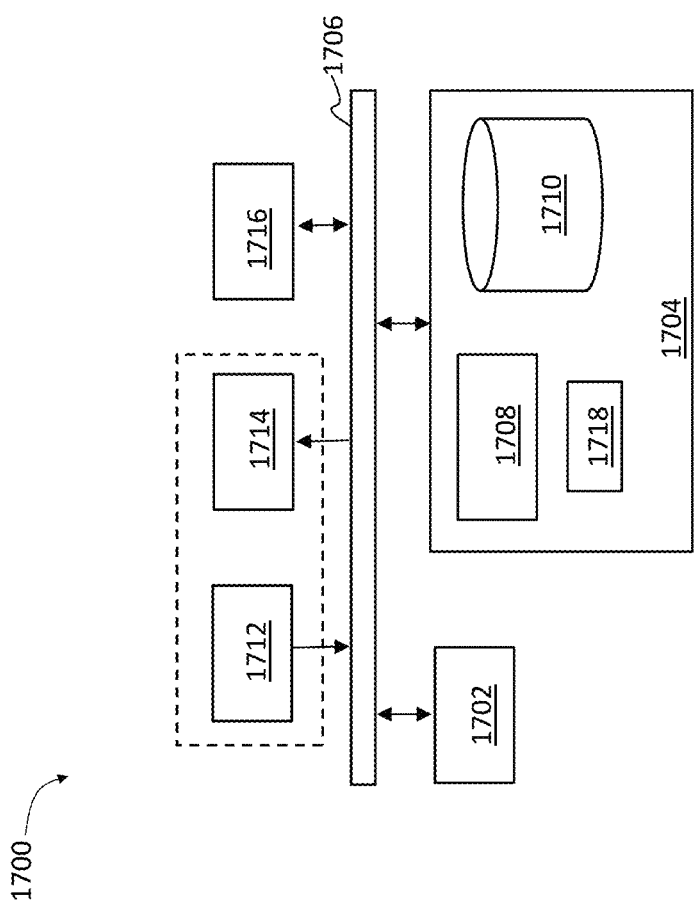
FIG. 17 provides a block diagram illustrating an example data processing system for carrying out molecular evaluation of a sample analyte using any of the nanogap sensors disclosed herein, according to some embodiments of the disclosure.

FIG. 17 provides a block diagram illustrating an example data processing system for carrying out molecular evaluation of a sample analyte using any of the nanogap sensors disclosed herein, according to some embodiments of the disclosure.

Such a data processing system could be configured to e.g., function as the sensor logic 110 described herein or as any other system configured to implement various improved mechanisms related to molecular evaluation of sample analytes using any of the nanogap sensors and arrangements of such sensors disclosed herein.

As shown in FIG. 17, the data processing system 1700 may include at least one processor 1702 coupled to memory elements 1704 through a system bus 1706. As such, the data processing system may store program code within memory elements 1704. Further, the processor 1702 may execute the program code accessed from the memory elements 1704 via a system bus 1706. In one aspect, the data processing system may be implemented as a computer that is suitable for storing and/or executing program code. It should be appreciated, however, that the data processing system 1700 may be implemented in the form of any system including a processor and a memory that is capable of performing the functions described within the disclosure.

The memory elements 1704 may include one or more physical memory devices such as, for example, local memory 1708 and one or more bulk storage devices 1710. The local memory may refer to RAM or other non-persistent memory device(s) generally used during actual execution of the program code. A bulk storage device may be implemented as a hard drive or other persistent data storage device. The processing system 1700 may also include one or more cache memories (not shown) that provide temporary storage of at least some program code in order to reduce the number of times program code must be retrieved from the bulk storage device 1710 during execution.

Input/output (I/O) devices depicted as an input device 1712 and an output device 1714, optionally, can be coupled to the data processing system. Examples of input devices may include, but are not limited to, a keyboard, a pointing device such as a mouse, or the like. Examples of output devices may include, but are not limited to, a monitor or a display, speakers, or the like. Input and/or output devices may be coupled to the data processing system either directly or through intervening I/O controllers.

In an embodiment, the input and the output devices may be implemented as a combined input/output device (illustrated in FIG. 17 with a dashed line surrounding the input device 1712 and the output device 1714). An example of such a combined device is a touch sensitive display, also sometimes referred to as a "touch screen display" or simply "touch screen". In such an embodiment, input to the device may be provided by a movement of a physical object, such as e.g., a stylus or a finger of a user, on or near the touch screen display.

A network adapter 1716 may also, optionally, be coupled to the data processing system to enable it to become coupled to other systems, computer systems, remote network devices, and/or remote storage devices through intervening private or public networks. The network adapter may comprise a data receiver for receiving data that is transmitted by said systems, devices and/or networks to the data processing system 1700, and a data transmitter for transmitting data from the data processing system 1700 to said systems, devices and/or networks. Modems, cable modems, and Ethernet cards are examples of different types of network adapter that may be used with the data processing system 1700.

As pictured in FIG. 17, the memory elements 1704 may store an application 1718. In various embodiments, the application 1718 may be stored in the local memory 1708, the one or more bulk storage devices 1710, or apart from the local memory and the bulk storage devices. It should be appreciated that the data processing system 1700 may further execute an operating system (not shown in FIG. 17) that can facilitate execution of the application 1718. The application 1718, being implemented in the form of executable program code, can be executed by the data processing system 1700, e.g., by the processor 1702. Responsive to executing the application, the data processing system 1700 may be configured to perform one or more operations or method steps described herein.

Variations and Implementations

In the discussions of the embodiments above, sensors, capacitors, comparators, amplifiers, switches, digital core, transistors, and/or other components can readily be replaced, substituted, or otherwise modified in order to accommodate particular circuitry needs implementing molecular evaluation of sample analytes using any of the nanogap sensors and arrangements of such sensors disclosed herein. Moreover, it should be noted that the use of complementary electronic devices, hardware, software, etc. offer an equally viable option for implementing the teachings of the disclosure.

In one example embodiment, any number of electrical circuits for implementing any of the nanogap sensors and arrangements of such sensors disclosed herein, described herein, may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of DSPs, microprocessors, supporting chipsets, etc.), computer-readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In various embodiments, the functionalities of any of the nanogap sensors and arrangements of such sensors disclosed herein may be implemented in emulation form as software or firmware running within one or more configurable (e.g., programmable) elements arranged in a structure that supports these functions. The software or firmware providing the emulation may be provided on non-transitory computer-readable storage medium comprising instructions to allow a processor to carry out those functionalities.

In another example embodiment, the electrical circuits of the FIGS. may be implemented as stand-alone modules (e.g., a device with associated components and circuitry configured to perform a specific application or function) or implemented as plug-in modules into application specific hardware of electronic devices. Note that various embodiments related to the nanogap sensors and arrangements of such sensors disclosed herein may be readily included in a system on chip (SOC) package, either in part, or in whole. An SOC represents an IC that integrates components of a computer or other electronic system into a single chip. It may contain digital, analog, mixed-signal, and often radio frequency functions: all of which may be provided on a single chip substrate. Other embodiments may include a multi-chip-module (MCM), with a plurality of separate ICs located within a single electronic package and configured to interact closely with each other through the electronic package. In various other embodiments, any of the nanogap sensors and arrangements of such sensors disclosed herein may be implemented in one or more silicon cores in ASICs, FPGAs, and other semiconductor chips.

It is also imperative to note that all of the specifications, dimensions, and relationships related to molecular evaluation of sample analytes using any of the nanogap sensors and arrangements of such sensors outlined herein (e.g., the number and the order of fabrication steps, the number of components, etc.) have only been offered for purposes of example and teaching only. Such information may be varied considerably without departing from the spirit of the disclosure, or the scope of the appended claims. The specifications apply only to some non-limiting examples and, accordingly, they should be construed as such. In the foregoing description, example embodiments have been described with reference to particular method steps and/or component arrangements. Various modifications and changes may be made to such embodiments without departing from the scope of the appended claims. The description and drawings are, accordingly, to be regarded in an illustrative rather than in a restrictive sense.

Note that the activities discussed above with reference to the FIGS. are applicable to any ICs that involve signal processing associated with molecular evaluation of sample analytes using nanogap sensors, particularly those that can execute specialized software programs, or algorithms, some of which may be associated with converting an analog signal to a digital signal and processing such digital signal. Certain embodiments can relate to multi-DSP signal processing, floating point processing, signal/control processing, fixed-function processing, microcontroller applications, etc. In certain contexts, the features discussed herein can be applicable to medical systems, scientific instrumentation, wireless and wired communications, radar, industrial process control, audio and video equipment, current sensing, instrumentation (which can be highly precise), and other digital-processing-based systems utilizing molecular evaluation of sample analytes using nanogap sensors. Moreover, certain embodiments discussed above can be provisioned in digital signal processing technologies for medical imaging, patient monitoring, medical instrumentation, and home healthcare. This could include pulmonary monitors, accelerometers, heart rate monitors, pacemakers, etc. Other applications can involve automotive technologies for safety systems (e.g., stability control systems, driver assistance systems, braking systems, infotainment and interior applications of any kind). In yet other example scenarios, the teachings of the disclosure can be applicable in the industrial markets that include process control systems that help drive productivity, energy efficiency, and reliability. In consumer applications, the teachings of the molecular evaluation of sample analytes using any of the nanogap sensors and arrangements of such sensors discussed above can be used for products related to personal biotesting.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGS. may be combined in various possible configurations, all of which are clearly within the broad scope of the disclosure. In certain cases, it may be easier to describe one or more of the functionalities of a given set of flows by only referencing a limited number of electrical elements. It should be appreciated that the electrical circuits of the FIGS. and its teachings are readily scalable and can accommodate a larger number of components, as well as more complicated/sophisticated arrangements and configurations.

Accordingly, the examples provided should not limit the scope or inhibit the broad teachings of the electrical circuits as potentially applied to a myriad of other architectures.

Note that in the disclosure, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the disclosure, but may or may not necessarily be combined in the same or other embodiments.

It is also important to note that the functions related to molecular evaluation of sample analytes using any of the nanogap sensors and arrangements of such sensors disclosed herein illustrate only some of the possible functions that may be executed by, or within, systems illustrated in the FIGS. Some of these operations may be deleted or removed where appropriate, or these operations may be modified or changed considerably without departing from the scope of the disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the disclosure.

Numerous other changes, substitutions, variations, alterations, and modifications may be ascertained to one skilled in the art and it is intended that the disclosure encompass all such changes, substitutions, variations, alterations, and modifications as falling within the scope of the appended claims. Note that all optional features of the apparatus described above may also be implemented with respect to the method or process described herein and specifics in the examples may be used anywhere in one or more embodiments.

Parts of various apparatuses for molecular evaluation of sample analytes using any of the nanogap sensors and arrangements of such sensors disclosed herein can include electronic circuitry to perform the functions described herein. In some cases, one or more parts of the apparatus can be provided by a processor specially configured for carrying out the functions described herein. For instance, the processor may include one or more application specific components, or may include programmable logic gates which are configured to carry out the functions describe herein. The circuitry can operate in analog domain, digital domain, or in a mixed signal domain. In some instances, the processor may be configured to carrying out the functions described herein by executing one or more instructions stored on a non-transitory computer medium.

Note that all optional features of the apparatus described above may also be implemented with respect to the method or process described herein and specifics in the examples may be used anywhere in one or more embodiments.

Select Examples

Example A1 provides a nanogap sensor arrangement as shown in FIG. 2A. Example A2 provides a nanogap sensor arrangement as shown in FIG. 3. Example A3 provides an array of nanogap sensors as shown in FIGS. 5A-5C. Example A4 provides a nanogap sensor arrangement as shown in FIG. 6. Example A5 provides a plurality of nanogap sensors arranged as shown in FIGS. 7A-7B. Example A6 provides a nanogap sensor arrangement as shown in FIG. 3. Example A7 provides an array of nanogap sensors as shown in FIG. 8. Example A8 provides an array of nanogap sensors as shown in FIG. 9. Example A9 provides an array of nanogap sensors as shown in FIG. 10. Example A10 provides an array of nanogap sensors as shown in FIG. 11. Example A11 provides a nanogap sensor arrangement as shown in FIG. 12. Example A12 provides a nanogap sensor arrangement as shown in FIG. 13C. Example A13 provides a nanogap sensor arrangement as shown in FIG. 14C. Example A14 provides a nanogap sensor arrangement as shown in FIG. 15. Example A15 provides an array of nanogap sensors as shown in FIG. 16. Example A16 provides a nanogap sensor arrangement as shown in FIG. 12. Example A17 provides a nanogap sensor arrangement as shown in FIG. 12. Examples A18 provides methods for fabricating nanogap sensor arrangements and nanogap sensor arrays according to any one of the preceding Examples. Example A19 provides systems for evaluation of molecular content of various analytes using nanogap sensor arrangements and nanogap sensor arrays according to any one of the preceding Examples.

Example B1 provides a transducer device for analyzing one or more fluid analytes, the transducer device including a nanogap sensor provided over a substrate, the nanogap sensor including a first electrode and a second electrode, the second electrode opposite the first electrode and separated from the first electrode by a nanogap, where each of the first electrode and the second electrode is substantially parallel to the substrate; a first interconnect configured to provide electrical connectivity to the first electrode; and a second interconnect configured to provide electrical connectivity to the second electrode. In the transducer device of example B1, the first interconnect is in a first layer over the substrate, the nanogap sensor is in a second layer over the substrate, and the second interconnect is in a third layer over the substrate, the second layer being between the first layer and the third layer, and the first layer being between the substrate and the second layer.

Example B2 provides a transducer device similar to that of example B1, but, in the transducer device of example B2, both the first interconnect and the second interconnect are between the substrate and the sensor.

Example B3 provides the transducer device according to examples B1 or B2, where at least a portion of the second electrode forms a cantilever at least partially suspended over at least a portion of the first electrode.

Example B4 provides the transducer device according to examples B1 or B2, where at least a portion of the second electrode forms a bridge over at least a portion of the first electrode.

Example B5 provides the transducer device according to any one of the preceding examples B, further including a solid dielectric material between at least a portion of the second electrode and at least a portion of the first electrode. In some embodiments, such a dielectric material may provide mechanical support for the second electrode shaped as a cantilever or as a bridge, at least partially suspended over the first electrode. In some embodiments, such a dielectric material may be the left over of the sacrificial material used to form the nanogap.

Example B6 provides the transducer device according to any one of the preceding examples B, where a mean surface roughness of at least a portion of the first electrode is less than about 10 nm.

Example B7 provides the transducer device according to any one of the preceding examples B, where the nanogap is oriented substantially horizontally with respect to the substrate.

Example B8 provides the transducer device according to any one of the preceding examples B, where a distance between the first and second electrodes (i.e., the height of the horizontal nanogap) is between about 1 and 100 nm, including all values and ranges therein, e.g. between about 2 and 50 nm, or between about 5 and 20 nm.

Example B9 provides the transducer device according to any one of the preceding examples B, further including a first layer disposed over at least a portion of the first electrode, the first layer being a molecular layer, including one or more thiols, dithiols, or alkanethiols.

Example B10 provides the transducer device according to any one of the preceding examples B, further including a second layer disposed over at least a portion of the second electrode, the second layer including one or more thiols, dithiols, or alkanethiols.

Example B11 provides the transducer device according to any one of the preceding examples B, further including one or more fluidic windows configured to support provision of the fluid analyte(s) to the nanogap.

Example B12 provides a method for fabricating a nanogap sensor, the method including forming a first opening in a non-conductive (e.g., an insulator) layer provided over a substrate; depositing a spacer layer within the first opening (e.g., depositing the spacer layer as a liner provided on inner sidewalls and bottom of the first opening); forming a second opening in the non-conductive layer by removing at least a portion of the non-conductive layer adjacent to at least a portion of the spacer layer; forming a first electrode by depositing a first electrode material within the first opening having the spacer layer deposited therein; forming a second electrode by depositing a second electrode material within the second opening; and removing the portion of the spacer layer to form a nanogap between the first electrode and the second electrode.

Example B13 provides the method according to example B12, where the spacer layer is deposited within the opening in the non-conductive layer using a conformal deposition process, e.g. using ALD.

Example B14 provides the method according to examples B12 or B13, where the first opening is a rectangular (e.g., square) or a hexagonal opening.

Example B15 provides the method according to any one of examples B12-14, where a width of the nanogap (i.e., the distance between the first electrode and the second electrode) is between about 1 and 100 nm, including all values and ranges therein, e.g. between about 2 and 50 nm, or between about 5 and 20 nm.

Example B16 provides the method according to any one of examples B12-15, where the first electrode material and the second electrode material have substantially the same material composition. Such electrodes may be provided in a single deposition process that fills the first and second openings substantially at the same time, as illustrated with the following example.

Example B17 provides the method according to example B16, where the first electrode material is deposited substantially simultaneously with the second electrode material.

Example B18 provides the method according to any one of examples B12-15, where the first electrode material is different from the second electrode material. Such electrodes may be provided in two different processes and may, optionally, use lithographic and masking techniques to selectively deposit the first electrode material only substantially in the first opening and the second electrode material only substantially in the second opening.

Example B19 provides the method according to any one of examples B12-18, where the nanogap is oriented at an angle between about 85 and 95 degrees with respect to the substrate.

Example B20 provides the method according to any one of examples B12-19, where the first opening has a substantially re-entrant profile where a width at the top of the first opening is smaller than the width at the bottom of the first opening.

Example B21 provides the method according to example B20, where depositing the first electrode material within the first opening leaves a first volume within the first opening without the first electrode material deposited therein, the first volume being in a region of the first opening where a sidewall of the first opening meets a bottom of the first opening.

Example B22 provides the method according to any one of examples B12-19, where the first opening has a substantially non-re-entrant profile where a width at the top of the first opening is larger than the width at the bottom of the first opening.

Example B23 provides the method according to example B22, where depositing the second electrode material within the second opening leaves a second volume within the second opening without the second electrode material deposited therein, the second volume being in a region of the non-conductive layer where a sidewall of the first opening meets a bottom of the first opening.

Example B24 provides the method according to any one of examples B12-23, further including providing a first layer over at least a portion of the first electrode that is opposite at least a portion of the second electrode, the first layer including a material to which molecules of an analyte to be analyzed are to be attached during operation of the nanogap sensor.

Example B25 provides the method according to example B24, where the first layer includes one or more of thiols, e.g., monothiols, dithiols, alkanethiols such as mercapto-propanol or mercaptohexanol.

Example B26 provides the method according to any one of examples B12-25, further including providing a second layer over at least a portion of the second electrode that is opposite at least a portion of the first electrode, the second layer including a material to which molecules of an analyte to be analyzed are to be attached during operation of the nanogap sensor.

Example B27 provides the method according to example B26, where the first layer includes one or more of thiols, dithiols, or alkanethiols.

Example B28 provides a method for fabricating a nanogap sensor, the method including forming a first opening in a non-conductive (e.g., an insulator) layer provided over a substrate; depositing a sacrificial material within the first opening (e.g., filling the first opening with the sacrificial material); forming a second opening in the sacrificial material by removing a first portion of the sacrificial material; depositing a spacer layer within the second opening (e.g., depositing the spacer layer as a liner provided on inner sidewalls and bottom of the second opening); forming a first electrode by depositing a first electrode material within the second opening having the spacer layer deposited therein; forming a third opening in the sacrificial material by removing a second portion of the sacrificial material adjacent to at least a portion of the spacer layer; forming a second electrode by depositing a second electrode material within the third opening; and removing the portion of the spacer layer to form a nanogap between the first electrode and the second electrode.

Example B29 provides the method according to example B28, where a mean surface roughness (RA) of at least a portion of the first electrode opposite the second electrode is less than about 10 nm.

Example B30 provides the method according to examples B28 or B29, where the second electrode is formed after the first electrode is formed.

Example B31 provides the method according to any one of examples B28-B30, further including providing a first layer over at least a portion of the first electrode that is opposite at least a portion of the second electrode, the first layer including a material to which molecules of an analyte to be analyzed are to be attached during operation of the nanogap sensor.

Example B32 provides the method according to example B31, where the first layer includes one or more of alkanethiols.

Example B33 provides the method according to any one of examples B28-32, further including providing a second layer over at least a portion of the second electrode that is opposite at least a portion of the first electrode, the second layer including a material to which molecules of an analyte to be analyzed are to be attached during operation of the nanogap sensor.

Example B34 provides the method according to example B33, where the first layer includes one or more of thiols, dithiols, or alkanethiols.

Example B35 provides a method for fabricating a nanogap sensor, the method including forming a first opening in a non-conductive (e.g., an insulator) layer provided over a substrate; forming a first electrode by depositing a first electrode material within the first opening; forming a second opening in the first electrode material, the second opening extending through the first electrode material past a bottom of the first opening; depositing a spacer layer within the second opening (e.g., depositing the spacer layer as a liner provided on inner sidewalls and bottom of the second opening); forming a second electrode by depositing a second electrode material within the second opening having the spacer layer deposited therein; and removing at least a portion of the spacer layer to form a nanogap between the first electrode and the second electrode.

Example B36 provides the method according to example B35, where the spacer layer is deposited within the second opening using a conformal deposition process, e.g. using ALD.

Example B37 provides the method according to examples B35 or B36, where the second opening is a rectangular (e.g., square) or a hexagonal opening.

Example B38 provides the method according to any one of examples B35-37, where a width of the nanogap (i.e., the distance between the first electrode and the second electrode) is between about 1 and 100 nm, including all values and ranges therein, e.g. between about 2 and 50 nm, or between about 5 and 20 nm.

Example B39 provides the method according to any one of examples B35-38, further including providing a first layer over at least a portion of the first electrode that is opposite at least a portion of the second electrode, the first layer including a material to which molecules of an analyte to be analyzed are to be attached during operation of the nanogap sensor.

Example B40 provides the method according to example B39, where the first layer includes one or more of alkanethiols.

Example B41 provides the method according to any one of examples B35-40, further including providing a second layer over at least a portion of the second electrode that is opposite at least a portion of the first electrode, the second layer including a material to which molecules of an analyte to be analyzed are to be attached during operation of the nanogap sensor.

Example B42 provides the method according to example B41, where the first layer includes one or more of thiols, dithiols, or alkanethiols.

Example C1 provides a transducer device for analyzing molecular content of one or more fluid analytes using an array of nanogap sensors, the device including a plurality of first metal lines; and a plurality of second metal lines; where the first metal lines and the second metal lines are arranged in a grid as to form a plurality of nanogap sensors, where an individual nanogap sensor of the plurality of nanogap sensors includes a unique/respective combination of a first electrode formed by a portion of one of the plurality of the first metal lines and a second electrode formed by a portion of one of the plurality of the second metal lines, the second electrode being opposite the first electrode and separated from the first electrode by a nanogap. As used herein, the term "unique/respective combination" refers to a combination of a first and second electrodes such that no two nanogap sensors share both one of the plurality of first metal lines and one of the plurality of second metal lines. In other words, each nanogap sensor is formed by a respective different combination of one of the plurality of first metal lines and one of the plurality of second metal lines. For example, if a first plurality of nanogap sensors are formed with the same one of the plurality of first metal lines, then each of such nanogap sensors includes a different one of the plurality of second metal lines; similarly, if a second plurality of nanogap sensors are formed with the same one of the plurality of second metal lines, then each of such nanogap sensors includes a different one of the plurality of first metal lines.

Example C2 provides the transducer device according to example C1, where the portion of one of the plurality of the second metal lines of the individual nanogap sensor forms a bridge over the portion of one of the plurality of the first metal lines.

Example C3 provides the transducer device according to example C2, further including a solid dielectric material between the first electrode and the second electrode. In some embodiments, such a solid dielectric material may provide mechanical support for the second electrode shaped as a bridge suspended over the first electrode. In some embodiments, such a solid dielectric material may be the left overs of the sacrificial material used to form the nanogap.

Example C4 provides the transducer device according to any one of the preceding examples C, where a mean surface roughness of at least a portion of the first electrode of the individual nanogap sensor is less than about 10, or less than about 5, nanometers.

Example C5 provides the transducer device according to any one of the preceding examples C, where the nanogap is oriented substantially horizontally with respect to a substrate over which the plurality of first metal lines and the plurality of second metal lines are provided.

Example C6 provides the transducer device according to any one of the preceding examples C, where the plurality of nanogap sensors are horizontal nanogap sensors arranged in rows and columns.

Example D1 provides a transducer device for analyzing a molecular content of one or more fluid analytes using an array of nanogap sensors, the device including a first metal line, forming a common/shared first electrode for each of a plurality of nanogap sensors (thus, the first electrodes of these sensors are formed of an electrically continuous metal line); and an individual different second electrode for each of the plurality of nanogap sensors; where an individual nanogap sensor of the plurality of nanogap sensors includes a first electrode formed by a respective/different portion of the first metal line (or, in other words, of the common/shared first electrode) opposite the individual second electrode and separated from the individual second electrode by a nanogap.

Example D2 provides the transducer device according to example D1, where the nanogap is oriented substantially at an angle between about 85 and 95 degrees with respect to the substrate.

Example D3 provides the transducer device according to examples D1 or D2, where the first metal line is one of a plurality of first metal lines, the plurality of nanogap sensors is one subset of a plurality of subsets of nanogap sensors arranged along different ones of the plurality of first metal lines, and the nanogap sensors of the plurality of subsets of nanogap sensors are vertical nanogap sensors arranged in rows and columns.

Example D4 provides the transducer device according to any one of the preceding examples D, further including a third electrode for each of the plurality of nanogap sensors. Such a third electrode may be configured to serve as a noise shield by being connected to a certain potential, e.g., a ground potential, during operation of the electronic device.

Example D5 provides the transducer device according to example D4, where the third electrodes for the plurality of nanogap sensors are formed of respective/different portion of a third metal line (in other words, the third metal line forms a common/shared third electrode for each of the plurality of nanogap sensors), Example D6 provides the transducer device according to example D5, where the first metal line is substantially parallel to the third metal line.

Example D7 provides the transducer device according to any one of examples D4-D6, where, in a top down view of the array of nanogap sensors, for each of the plurality of nanogap sensors, the second electrode is between the first electrode and the third electrode.

Example D8 provides the transducer device according to any one of examples D4-D7, further including a solid dielectric material between the second electrode and the third electrode.

Example D9 provides the transducer device according to example D8, further including the solid dielectric material between at least a portion of the second electrode and the substrate (in other words, the solid dielectric material that separates the second electrode from the third electrode may extend further to be under at least a portion of the second electrode).

Example D10 provides the transducer device according to examples D8 or D9, where the solid dielectric material is in contact with the second electrode.

Example E1 provides a transducer device for analyzing molecular content of one or more fluid analytes using an array of nanogap sensors, the device including a plurality of nanogap sensors, each nanogap sensor including a first electrode and a second electrode, where the second electrode is a single common/shared electrode for the plurality of nanogap sensors, the first electrode is opposite the second electrode and separated from the second electrode by a respective different nanogap, and the first electrodes of the plurality of nanogap sensors are arranged along a closed contour.

Example E2 provides the transducer device according to example E1, where the closed contour is a hexagon and the plurality of nanogap sensors includes 6 nanogap sensors. Example E3 provides the transducer device according to example E1, where the closed contour is a rectangle and the plurality of nanogap sensors includes 4 nanogap sensors. Example E4 provides the transducer device according to example E1, where the closed contour is a triangle and the plurality of nanogap sensors includes 3 nanogap sensors. Example E5 provides the transducer device according to any one of the preceding examples E, where the nanogap is oriented substantially at an angle between about 85 and 95 degrees with respect to a substrate over which the first metal line is provided.

The invention claimed is:

1. A transducer device for analyzing one or more fluid analytes, the transducer device comprising:
    a nanogap sensor over a substrate, the nanogap sensor including a first electrode having a planar shape and a second electrode, the second electrode opposite the first electrode and separated from the first electrode by a nanogap for receiving a liquid analyte, wherein each of the first electrode and the second electrode is parallel to the substrate;
    a first interconnect configured to provide electrical connectivity to the first electrode; and
    a second interconnect configured to provide electrical connectivity to the second electrode,
    wherein:
    at least a portion of the second electrode forms a planar, fully-released cantilever suspended directly over at least a majority of the first electrode,
    the planar shape of the first electrode and the planar shape of the fully-released cantilever are parallel to one another and function as a parallel plate capacitor;
    the first interconnect is in a first layer over the substrate,
    the nanogap sensor is in a second layer over the substrate, and
    the second interconnect is in a third layer over the substrate, the second layer being between the first layer and the third layer, and the first layer being between the substrate and the second layer.

2. The transducer device according to claim 1, wherein at least a portion of the second electrode forms a structure resembling a projecting beam over at least a portion of the first electrode.

3. The transducer device according to claim 1, further comprising a solid dielectric material between at least a portion of the second electrode and at least a portion of the first electrode.

4. The transducer device according to claim 1, wherein a mean surface roughness of the first electrode is less than 10 nm.

5. The transducer device according to claim 1, wherein the nanogap is oriented horizontally with respect to the substrate.

6. The transducer device according to claim 1, wherein a distance between the first electrode and the second electrode is between 1 and 100 nm.

7. The transducer device according to claim 1, further comprising a first layer disposed over at least a portion of the first electrode, the first layer including one or more thiols, dithiols, or alkanethiols.

8. The transducer device according to claim 1, further comprising a second layer disposed over at least a portion of the second electrode, the second layer including one or more thiols, dithiols, or alkanethiols.

9. The transducer device according to claim 1, further comprising one or more fluidic windows configured to support provision of the one or more fluid analytes to the nanogap.

10. A transducer device for analyzing one or more fluid analytes, the transducer device comprising:
- a nanogap sensor over a substrate, the nanogap sensor including a first electrode having a planar shape and a second electrode, the second electrode opposite the first electrode and separated from the first electrode by a nanogap for receiving a liquid analyte, wherein each of the first electrode and the second electrode is parallel to the substrate;
- a first interconnect configured to provide electrical connectivity to the first electrode; and
- a second interconnect configured to provide electrical connectivity to the second electrode, wherein:
- both the first interconnect and the second interconnect are between the substrate and the nanogap sensor;
- at least a portion of the second electrode forms a planar, fully-released cantilever directly suspended over at least a majority of the first electrode, and
- the planar shape of the first electrode and the planar shape of the fully-released cantilever are parallel to one another and function as a parallel plate capacitor.

11. The transducer device according to claim 10, wherein at least a portion of the second electrode forms a structure resembling a projecting beam over at least a portion of the first electrode.

12. The transducer device according to claim 10, further comprising a solid dielectric material between at least a portion of the second electrode and at least a portion of the first electrode.

13. The transducer device according to claim 10, wherein a mean surface roughness of the first electrode is less than 10 nm.

14. The transducer device according to claim 10, wherein the nanogap is oriented horizontally with respect to the substrate.

15. The transducer device according to claim 10, wherein a distance between the first electrode and the second electrode is between 1 and 100 nm.

16. The transducer device according to claim 10, further comprising a first layer disposed over at least a portion of the first electrode, the first layer including one or more thiols, dithiols, or alkanethiols.

17. The transducer device according to claim 10, further comprising a second layer disposed over at least a portion of the second electrode, the second layer including one or more thiols, dithiols, or alkanethiols.

18. The transducer device according to claim 10, further comprising one or more fluidic windows configured to support provision of the one or more fluid analytes to the nanogap.

* * * * *